(12) United States Patent
Sefton

(10) Patent No.: US 12,247,194 B2
(45) Date of Patent: Mar. 11, 2025

(54) BIOREACTORS WITH INTEGRATED CATALYTIC NITROGEN FIXATION

(71) Applicant: Oakbio, Inc., Emeryville, CA (US)

(72) Inventor: Brian Sefton, Cupertino, CA (US)

(73) Assignee: Oakbio, Inc., Emeryville, CA (US)

( * ) Notice: Subject to any disclaimer, the term of this patent is extended or adjusted under 35 U.S.C. 154(b) by 1077 days.

(21) Appl. No.: 17/100,216

(22) Filed: Nov. 20, 2020

(65) Prior Publication Data

US 2021/0147787 A1    May 20, 2021

Related U.S. Application Data

(63) Continuation of application No. PCT/US2020/061484, filed on Nov. 20, 2020.
(Continued)

(51) Int. Cl.
| | |
|---|---|
| C12M 1/00 | (2006.01) |
| B01J 19/24 | (2006.01) |
| C01B 3/02 | (2006.01) |
| C01B 3/48 | (2006.01) |
| C01B 32/40 | (2017.01) |
| C01C 1/04 | (2006.01) |
| B01D 3/14 | (2006.01) |

(Continued)

(52) U.S. Cl.
CPC ........... *C12M 43/00* (2013.01); *B01J 19/245* (2013.01); *C01B 3/025* (2013.01); *C01B 3/48* (2013.01); *C01B 32/40* (2017.08); *C01C 1/0417* (2013.01); *C12M 29/00* (2013.01); B01D 3/14 (2013.01); B01D 53/047 (2013.01); B01J 2219/0004 (2013.01); C01B 2203/0233 (2013.01); C01B 2203/0283 (2013.01); C01B 2203/068 (2013.01); C25B 1/04 (2013.01)

(58) Field of Classification Search
CPC ............................. C12M 43/00; C01B 3/025
See application file for complete search history.

(56) References Cited

U.S. PATENT DOCUMENTS

| | | | |
|---|---|---|---|
| 3,426,543 A | 2/1969 | Becker | |
| 4,289,625 A * | 9/1981 | Tarman | C12P 5/023 210/603 |

(Continued)

FOREIGN PATENT DOCUMENTS

WO    2019/142199 A1    7/2019

OTHER PUBLICATIONS

PCT/2020/061484, ISR and WO dated Feb. 19, 2021.

*Primary Examiner* — Jonathan M Hurst
(74) *Attorney, Agent, or Firm* — Rimon Law, P.C.

(57) ABSTRACT

Nitrogen in a form suitable for feeding a population of microbes in a bioreactor is produced by reacting nitrogen gas and hydrogen gas to form ammonia plus an unreacted gas stream under conditions favorable to having little unreacted nitrogen gas in the unreacted gas stream. The ammonia, or a compound derived from the ammonia is fed to the microbes and the unreacted gas stream is optionally fed back into the reaction, or fed into the bioreactor. Oxygen can be produced, such as by electrolysis, and also provided to the microbes. Hydrogen from the electrolysis can be added to the hydrogen being reacted with nitrogen gas, and/or can be added to the bioreactor. Where nitrogen gas is produced from air separation, the residual gases can be another source of oxygen.

14 Claims, 12 Drawing Sheets

Related U.S. Application Data

(60) Provisional application No. 62/938,046, filed on Nov. 20, 2019.

(51) Int. Cl.
  *B01D 53/047* (2006.01)
  *C25B 1/04* (2021.01)

(56) References Cited

U.S. PATENT DOCUMENTS

| | | | | |
|---|---|---|---|---|
| 4,886,651 | A | * | 12/1989 | Patel ............... C01C 1/0488 518/703 |
| 5,772,731 | A | * | 6/1998 | Harrison ............ B01F 25/53 95/8 |
| 7,476,296 | B2 | * | 1/2009 | Appel ............... B04B 5/12 202/118 |
| 2008/0302669 | A1 | | 12/2008 | Peters et al. |
| 2014/0271379 | A1 | | 9/2014 | Heidel et al. |
| 2015/0037853 | A1 | | 2/2015 | Fischer et al. |
| 2017/0341942 | A1 | * | 11/2017 | Harper, Jr. ........... F01K 7/16 |
| 2017/0342450 | A1 | * | 11/2017 | Kishino ............. C12P 13/08 |
| 2018/0305743 | A1 | | 10/2018 | Ghylin |

* cited by examiner

BIOREACTORS WITH INTEGRATED CATALYTIC NITROGEN FIXATION

CROSS-REFERENCE TO RELATED APPLICATIONS

This application claims the benefit of U.S. provisional patent application No. 62/938,046 filed on Nov. 20, 2019, and is also a continuation of PCT application PCT/US20/61484 filed on Nov. 20, 2020, the disclosures of both are incorporated herein by reference.

BACKGROUND

Field of the Invention

The invention is in the field of bioproduction and fermentation and more specifically pertains to the efficient provision of resources to bioreactors.

Related Art

The field of bioproduction often relies on the growth of microbes in liquid media in bioreactors or fermenters. A significant area of cost and carbon footprint is the requirement of providing nitrogen in a soluble form to the microbes. A major source of nitrogen used in bioproduction is in the form of ammonia and its acid form, ammonium, often in the form of salts such as ammonium hydroxide, ammonium chloride, ammonium diphosphate, ammonium sulfate, as well as other forms of nitrogen such as urea. The primary method of industrial production of biologically usable nitrogen is via the Haber-Bosch process (hereafter the Haber process), in which atmospheric molecular nitrogen is reacted at high temperature and high pressure with hydrogen to form ammonia. As discussed further below, high temperatures and pressures are favored to drive the reaction to completion to fully utilize all of the hydrogen. The Haber process is practiced at very large scale and supplies large amounts of ammonia for use in fertilizers, bioproduction and as a chemical ingredient for a wide variety of products and processes. The production of ammonia via the Haber process is a major contributor to greenhouse gas because natural gas is the feedstock from which the hydrogen for the Haber process is produced.

A number of other chemicals are also derived from ammonia produced in the Haber process, including urea through a reaction of ammonia with $CO_2$, as well as ammonium sulfate and ammonium nitrate. These chemicals can also be used in bioreactor systems to supply critical nutrients in the form of nitrogen containing compounds as well as sulfur.

Cultivation of microbes in bioreactors often also requires the addition of soluble nitrogen compounds and these are often produced by the Haber process, or derived from ammonia produced by the Haber process. This is particularly true of the cultivation of autotrophic microbes which can be grown in bioreactors containing media which primarily consists of mineral salts.

In order to practice the Haber process using nitrogen from the atmosphere it is necessary to separate the nitrogen from the other gases of the atmosphere. This can be done by a number of methods, one of which is the fractional distillation of air. The separation of nitrogen from the air leaves a residual which comprises primarily oxygen, argon, carbon dioxide, trace gases and in many cases, a small fraction of residual nitrogen.

Gas Fermentation

Gas fermentation is a type of bioproduction where autotrophic organisms are grown using gases as a source of energy and carbon. These organisms are referred to as chemoautotrophic because they obtain their energy and carbon from inorganic sources. In hydrogen-based biosynthesis, molecular hydrogen ($H_2$) is supplied to microbes, and the microbes react the hydrogen with oxygen in a reaction mediated by hydrogenase enzymes, to obtain energy. Carbon sources can also be gases, and the energy to fix carbon oxides, such as carbon dioxide and carbon monoxide, is derived from the energy transduction provided by the action of the hydrogenases reaction of molecular hydrogen. In many, but not all cases, the microbes use the enzyme Ribulose-1,5-bisphosphate carboxylase/oxygenase (rubisco), to assimilate $CO_2$.

Hydrogen oxidizing bacteria, including but not limited to Knallgas-bacteria, are bacteria that oxidize hydrogen as a source of energy with oxygen as the final electron acceptor. There are both Gram positive and Gram negative Knallgas bacteria. Methylotrophic, methanogenic, and several other types of bacteria are also able to live at least partially by reacting molecular hydrogen.

Many organisms are capable of using hydrogen ($H_2$) as a source of energy. There are several mechanisms of anaerobic hydrogen oxidation (e.g. sulfate reducing bacteria, acetogenic bacteria, methanogenic bacteria). Hydrogen can also be used as an energy source aerobically in the Knallgas reaction:

$$2H_2 + O_2 \rightarrow 2H_2O + \text{energy}$$

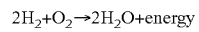

and in other reactions which provide energy in the form of reducing power to microbes such as the reduction of NADP to NADPH, or the formation of adenosine triphosphate, both of which are known to be mediated in many biological instances by hydrogenase enzymes. In others system hydrogen can be reacted to form formate, methanol or other molecules which microbes can then derive energy from.

In some organisms, hydrogen is oxidized by a membrane-bound hydrogenase causing proton pumping via electron transfer to various quinones and cytochromes. In many organisms, a second cytoplasmic hydrogenase is used to generate reducing power in the form of NADH, which is subsequently used to fix carbon dioxide via the Calvin cycle. Hydrogen-oxidizing organisms, such as *Cupriavidus necator* (formerly *Ralstonia eutropha*), or members of the genera *Hydrogenophaga, Rhodobacter, Rhodospirillium, Rhodococcus*, and many others often inhabit oxic-anoxic interfaces in nature to take advantage of the hydrogen produced by anaerobic fermentative organisms while still maintaining a supply of oxygen. Some of these can also function in anaerobic environments, as can many other species including many acetogens, which can utilize the reducing power of hydrogen as a source of energy while using a different terminal electron acceptor than oxygen. In some cases these anaerobic bacteria can produce compounds of value in the course of utilizing a final electron acceptor, for example, pyruvate in lactic acid fermentation or acetaldehyde in ethanol fermentation.

In some organisms various hydrogenase and other enzymes can function in such a way as to produce hydrogen. There are several pathways and metabolic modes for this. Dark fermentation is where microorganisms, such as certain bacteria, for example bacteria of the families Thermoanaerobacterales, Clostrodiaceae, and Enterobacteriaceae, as well as certain cyanobacteria, break down organic matter in the dark, in some cases resulting in the release of hydrogen. There are other phenomenon, for example, photoheterotrophic fermentation, where light energy is used by organisms for energy but their carbon source comes from the breakdown of organic compounds, and in some cases this leads to the release of hydrogen. This phenomenon is well known to be utilized by the purple non-sulfur bacteria (PNS). Hybrid systems, where for example, bacteria of the genera Clostridia break down organic matter to produce secondary metabolites such as fatty acids, or organic acids that are then broken down by other bacteria, sometimes in the presence of light, such as the PNS, produce hydrogen. Such systems can be arranged where the organisms are cultivated together (co-cultured), or where the steps outlined occur sequentially, such as by transferring the fermentation medium from one vessel with a population of microbes to a second vessel with a second population of microbes. Microbes may also be employed to produce hydrogen in artificial systems designed to facilitate this, For example, microbial fuel cells can be configured in such a way that the microbes, or cells, deposit electrons onto electrodes and cause the production of hydrogen at the counter electrode. Cell-free systems are also known in which enzymes mediate the production of hydrogen, either directly or indirectly.

Haber Process

The Haber process is an artificial nitrogen fixation process and is the main industrial procedure for the production of ammonia today. The process converts atmospheric nitrogen ($N_2$) to ammonia ($NH_3$) by a reaction with hydrogen ($H_2$) using a metal catalyst under high temperatures and pressures.

$$N_2 + 3H_2 \rightarrow 2NH_3$$

Nitrogen ($N_2$) is very unreactive because the molecules are held together by strong triple bonds. The Haber process relies on catalysts that accelerate the scission of this triple bond.

Two opposing considerations are relevant to this synthesis—the position of the equilibrium and the rate of reaction. At room temperature, the equilibrium is strongly in favor of ammonia, but the reaction doesn't proceed at a detectable rate. The obvious solution is to raise the temperature, but because the reaction is exothermic, the equilibrium constant (using bar or atm units) becomes 1 around 150-200° C. (302-392° F.). (See Le Châtelier's principle)

$Kp(T)$ for $N_2 + 3H_2 \rightleftharpoons NH_3$

| Temperature (° C.) | Kp |
|---|---|
| 300 | $4.34 \times 10^{-3}$ |
| 400 | $1.64 \times 10^{-4}$ |
| 450 | $4.51 \times 10^{-5}$ |
| 500 | $1.45 \times 10^{-5}$ |
| 550 | $5.38 \times 10^{-6}$ |
| 600 | $2.25 \times 10^{-6}$ |

Above the temperature at which the equilibrium constant becomes 1, the equilibrium quickly becomes quite unfavorable at atmospheric pressure, according to the van't Hoff equation. Thus, a low temperature coupled with some other means to increase reaction rate is desired. However, the catalyst itself requires a temperature of at least 400° C. to be efficient.

Pressure is the obvious choice to favor the forward reaction because there are 4 moles of reactant for every 2 moles of product, and the pressure used (15-25 MPa (150-250 bar; 2,200-3,600 psi)) alters the equilibrium concentrations to give a profitable yield.

Economically, pressurization of the reactor is expensive: pipes, valves, and reaction vessels need to be strengthened, and there are safety considerations when working at 15 MPa. In addition, running compressors takes considerable energy, as work must be done on the (very compressible) gas. Thus, the compromise used gives a single pass yield of around 15%.

Another way to increase the yield of the reaction would be to remove the product (i.e., ammonia gas) from the system. In practice, gaseous ammonia is not removed from the reactor itself, since the temperature is too high, it is removed from the equilibrium mixture of gases leaving the reaction vessel. The hot gases are cooled sufficiently, while maintaining a high pressure, for the ammonia to condense and be removed as a liquid. A stream comprising unreacted hydrogen and nitrogen gases are then returned to the reaction vessel to undergo further reaction.

FIG. 1 shows a schematic representation of an exemplary Haber reactor. The Haber reactor receives nitrogen and hydrogen separately, and mixes them prior to introduction into a compressor which increases the pressure of the gas mixture. The compressed gas mixture is introduced into a heated reactor vessel including a catalyst, in this example, an iron catalyst with a suitable promoter like $K_2O$, $CaO$, $SiO_2$, or $Al_2O_3$ at a temperature of 450° C. The reaction products exit the reactor vessel and pass into a cooling chamber where ammonia condenses out of the gas phase. The remaining gases, unreacted nitrogen and hydrogen, are recycled to the front end of the compressor. As a general principal of operation, the fixation of nitrogen into ammonia and other useful nitrogen containing compounds by the Haber process and other integrated processes is carried out at high temperature and pressure to increase the rate of reaction over efficiency. Economic losses from this lower efficiency are made up by a reduction in required plant size to produce quantities of nitrogenous product such as $NH_3$.

Other processes exist by which $NH_3$ is made from $H_2$ and $N_2$. Some of these involve membranes, some employ biocatalysts in the form of microorganisms or enzymes such as nitrogenases in cell-free or other systems. All of these methods involve the reaction of $H_2$ and $N_2$ into ammonia as an exothermic reaction and are thus similar, if not identical to the Haber process in stoichiometry.

SUMMARY

This invention provides methods to increase aerobic bioreactor efficiency by fixing nitrogen from atmospheric gas into ammonia while providing the bioreactor system with required oxygen rich gas streams as a by-product of the nitrogen fixation process. In the case of hydrogen based biosynthesis, and other gas fermentation technologies, this invention allows for production of ammonia on demand by first passing at least part of a hydrogen stream feedstock into an ammonia production system such as the Haber process, prior to entry to the bioreactor, and, in some embodiments, for increased efficiency by utilizing oxygen rich and $CO_2$ rich streams which are produced as side products of ammonia production.

The invention also provides for the collection of data for, and the control of the combined ammonia production and bioreactor system. Control can comprise predictive control, which can comprise machine learning and artificial intelligent control based on prior history and current sensor readings.

In some embodiments, the present invention provides a method to create a greatly reduced carbon footprint system where the nitrogen, oxygen and hydrogen gases needed for gas fermentation are produced from water and atmospheric gases with clean energy inputs. Exemplary systems and methods described herein that employ a Haber reactor or the Haber process will be understood to be representative species of the greater genus of ammonia production systems and methods.

The present invention provides systems where a water splitting technology such as a thermal, nuclear, catalytic or electrochemical process is used to split water into hydrogen and oxygen to provide hydrogen while producing little or no carbon emissions. For example, an electrolyzer powered by renewable energy produces hydrogen via the electrolysis of water. This hydrogen is fed into a Haber reactor which produces ammonia which is then fed into a bioreactor. The system thereby operates with a greatly reduced carbon footprint as compared to those systems that produce ammonia or ammonium from hydrogen derived from natural gas or methane. In these water splitting systems, the side product oxygen can also be at least partly fed into the bioreactor to supply oxygen required for aerobic processes.

The present invention also applies to other hydrogen oxidizing microbes which are classified differently than the Knallgas bacteria, but which can also engage in hydrogen oxidizing or hydrogen assisted metabolism. Examples of these are the methanogens, methane oxidizing microbes, organisms capable of chemoheterotrophic metabolism, carboxydotrophic microbes, some photoautotrophic microbes such as the purple non-sulfur bacteria (PNS), sulfur bacteria, acetogens and other microbes which can oxidize hydrogen to obtain energy but which may be known for other metabolic modes such as archaea, cyanobacteria, algae, yeasts and fungi. This invention also applies to yeasts or other microbes, plants or cells engineered to enhance or confer hydrogen oxidizing capabilities.

The present invention is intended to cover other processes where $H_2$ and $N_2$ are reacted to form $NH_3$ in addition to those strictly defined as the 'Haber' process. Other processes exist by which $NH_3$ is made from $H_2$ and $N_2$. Some of these involve membranes, some employ biocatalysts in the form of microorganisms or enzymes such as nitrogenases in cell-free or other systems. All of these methods involve the reaction of $H_2$ and $N_2$ into ammonia as an exothermic reaction and are thus similar, if not identical to the Haber process in stoichiometry.

DETAILED DESCRIPTION

Figure 1:
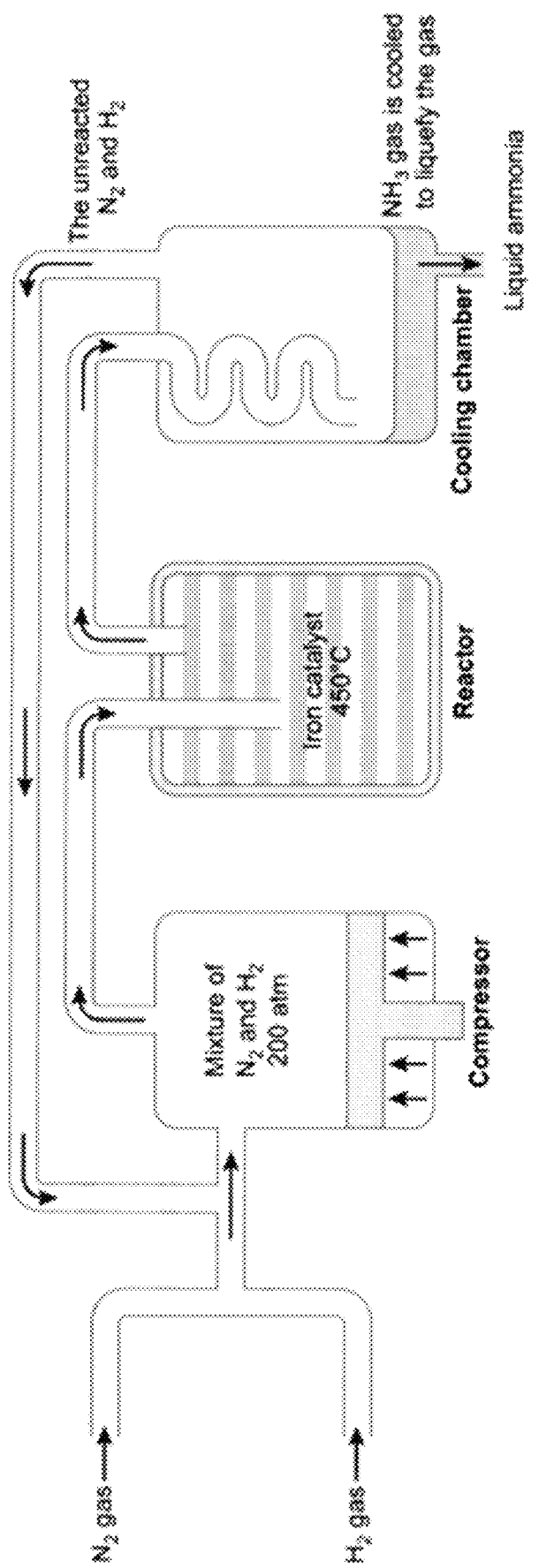
FIG. 1 is a schematic representation of an exemplary Haber reactor of the prior art.
Figure 2:
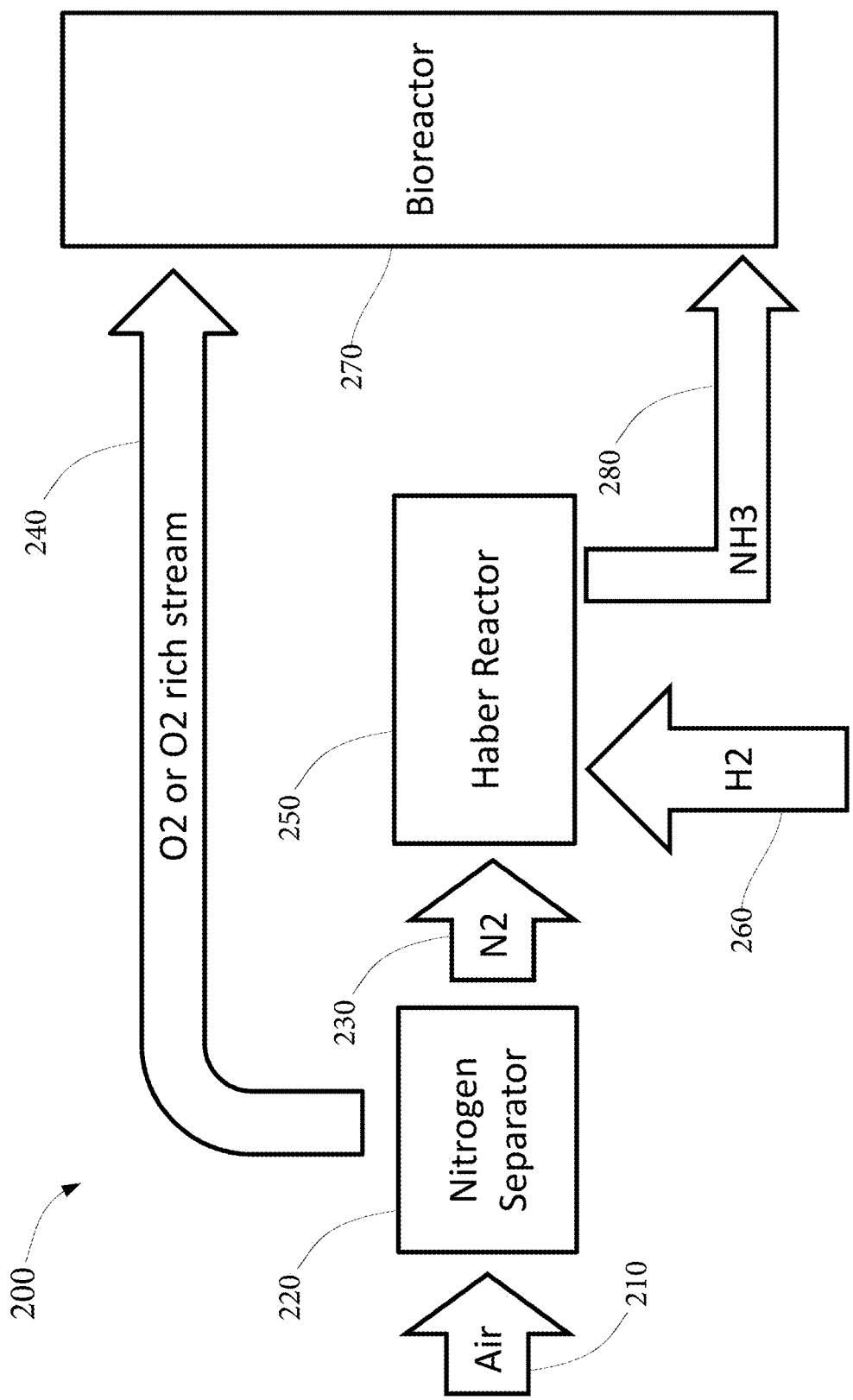
FIG. 2 is a schematic representation of an exemplary system according to various embodiments of the present invention.

FIG. 2 illustrates an exemplary system 200 in which air 210 is processed using a nitrogen separator 220 employing a nitrogen separation technology to produce a gaseous stream of nitrogen 230 and a residual gaseous stream 240 substantially of oxygen. At least some of the separated nitrogen is directed into a nitrogen fixation reactor 250 (referred to herein also as a Haber reactor) which also receives a stream of hydrogen 260, while the residual oxygen rich stream 240 is optionally directed into a bioreactor 270, depending on whether the microbes being cultivated require, or benefit from, the presence of oxygen. At least some of the 'fixed' nitrogen from the nitrogen separator 220, in the form of ammonia, ammonium, or other soluble form of nitrogen is directed into the bioreactor 270. As used herein, "Haber reactor 250" refers to the overall system of FIG. 1 from condenser to cooling chamber unless context indicates otherwise.

It will be appreciated that while the ammonia pathway 280 shows ammonia flowing directly from the Haber reactor 250 to the bioreactor 270, the pathway 280 represents both the direct flow from the Haber reactor 250 to the bioreactor 270 as well as indirect flow through further processing steps to generate other suitable nitrogen containing compounds from the ammonia. As used herein, "fluid communication" encompasses both direct flow between the end points as well as indirect flow that includes passing through one or more of valves, regulators, condensers, reservoirs, and chemical processing steps. Thus, the bioreactor 270 can be in fluid communication with the Haber reactor 250 through one or more chemical processing steps that convert the ammonia from the Haber reactor 250 into another fixed nitrogen compound derived from the ammonia stream. In this context, ammonia will be understood to be an example of a fixed nitrogen compound derived from the ammonia stream.

Any ammonia produced in the Haber reactor 250 but not immediately directed into the bioreactor 270 can be stored for later use (see FIG. 5) or directed to another use. It will be understood that in various embodiments the residual oxygen-rich stream 240 can be further fractionated to remove one or more residual gases and in this way create an oxygen rich stream with or without carbon dioxide, with or without carbon monoxide, with or without argon, and so forth, so better suit particular microbes. If the residual oxygen rich stream 240 contains some $CO_2$ or residual $N_2$, these might also be absorbed, or fixed by the autotrophic microbes, or, in other cases passed through the bioreactor 270.

In some embodiments, the ammonia that has been produced can be stored and later disassociated back to molecular hydrogen and molecular nitrogen. This reaction may be performed in a number of ways including spontaneously, via heating, via use of catalysts, or other methods. A method of separating the disassociated gases includes membrane based separation, selective adsorption using an adsorbent such as a zeolite, which in some cases may have a metal organic framework, or another selective adsorbent, selective reactivity, or other method to separate the nitrogen and hydrogen. Since the reverse of thirone Haber process, $2NH_3$ to $N_2+3H_2$, is endothermic, it can be used as a source of cooling or heat removal. In some embodiments this transition may be carried out in such a way as to provide cooling to a process by transferring heat to the reaction and thus cooling the process either directly, or indirectly via a heat exchanger. In further embodiments the ammonia is disassociated, and optionally used for cooling as described, but the resulting gases are not separated, instead the mixed gases are directed into the bioreactor 270.

The bioreactor 270, in these embodiments, comprises a vessel filled with a liquid medium in which a population of microbes is dispersed which are capable of using ammonia as a source of nitrogen. The liquid medium in the bioreactor 270 comprises a variety of chemical nutrients which supply the nutritional requirements of the microbes. These include but are not limited to phosphate, carbonate, chloride, iron, magnesium, manganese, cobalt, calcium, tungsten, selenium, bromine, sodium, nickel, protons, hydroxide, ammonia, ammonium, nitrate, nitrite, zinc, potassium, iodine, copper, and oxygen, in various forms, most of which are as charged ions.

The bioreactor vessel 270 comprises, in various embodiments, at least one sparger through which gases are added to the bioreactor 270. The bioreactor vessel 270 also comprises at least one liquid input port via which liquids can be added, at least one port through which gases can be vented, and at least one port through which the liquid medium can be withdrawn. The various ports of the bioreactor 270 may be controlled by valves which can be configured to allow the passage of material, block the passage of material or vary the amount of material which passes into or out of the bioreactor.

The Haber reactor 250 receives molecular nitrogen ($N_2$) from the nitrogen separator 220, and receives molecular hydrogen ($H_2$) 260 from a hydrogen source (not shown). Exemplary sources for feedstock hydrogen are described below. The nitrogen separator 220, in various embodiments, can employ fractional distillation, pressure swing adsorption, or any other suitable method, or combination of methods or steps, to concentrate nitrogen from the air.

As noted above, the Haber reactor 250 optionally comprises a catalyst and also comprises a heater to raise the temperature of the reactor 250 to a temperature higher than the external ambient temperature, and the reactor 250 can operate at a pressure greater than the ambient atmospheric pressure. In the exemplary Haber reactor shown in FIG. 1, employing an iron catalyst with a suitable promoter like $K_2O$, $CaO$, $SiO_2$, and $Al_2O_3$, or another catalyst, the gases are brought to a pressure of 200 atm and a temperature of 450° C. Inside the Haber reactor the $N_2$ and $H_2$ react to form ammonia ($NH_3$). A cooling chamber cools the resulting gases to the point where the ammonia will condense into a liquid. The liquid ammonia is then removed from the cooling chamber via a port and then conveyed either directly, or indirectly via a holding vessel (not shown), to the bioreactor 270. The movement of liquid ammonia into the bioreactor 270 may be assisted by a pump or other pressure source such as the elevated pressure inside the Haber reactor. Ammonia from the Haber reactor may also be further reacted to form other nitrogen-containing compounds, such as urea, and conveyed either directly, or indirectly via a holding vessel, to the bioreactor 270. Since in this invention it is not paramount to react hydrogen as completely as possible, a lower efficiency catalyst is preferable. Examples of such include an iron catalyst with a suitable promoter like $K_2O$, $CaO$, $SiO_2$, and $Al_2O_3$, and/or catalysts comprising Cr, Ru, Mn, Pt, and Pd. A suitable catalyst can additionally, or in the alternative comprise a biocatalyst such as one or more enzymes like a nitrogenase, and/or an organism which comprises at least one nitrogenase enzyme such as bacteria including cyanobacteria such as *Trichodesmium*, *Nostoc* and Cyanothece, green sulfur bacteria, Azotobacteraceae, *rhizobia* and *Frankia*, Clostridia, and Archea and others. Any catalyst which affects the reaction of $H_2$ and $N_2$ to form $NH_3$ potentially can be used. Also, no added catalyst may be used in some embodiments, as the reaction of $H_2$ and $N_2$ to form $NH_3$ can proceed without a catalyst.

The catalyst may be dispersed within the reactor as a coating, powder, or particle, or disposed within other particles such as a zeolite or other molecular sieve, and the catalyst can be incorporated into, or provided as, a porous structure, or impregnated on a membrane, or packed in a bed of a fluidized bed, or dispersed in a solution, or incorporated into biomass or any other type of support or structure. Moreover, the lower efficiency catalyst may be also comprised of a higher efficiency catalyst, but at a lower purity than used in high-efficiency ammonia production. Suitable catalysts can also comprise a mix of catalysts of varying efficiency. The advantage of some lower efficiency catalysts can be their lower costs.

In addition to, or in place of, the catalyst the reactor may comprise a molecular sieve or other material meant to increase the residency time of the respective gases in the reactor or their exposure to the catalyst or catalytic conditions from $NH_3$ formation.

It is noted that a Haber reactor 250 can be run differently when being used to manufacture ammonia to supply nitrogen to a bioreactor process because the bioreactor 270 does not have to be run continuously, or for maximum throughput, or in the case of supporting the culture of hydrogen oxidizing bacteria, for maximizing utilization of hydrogen. The factors of pressure, temperature and residence time thus can be different than those favored for the bulk industrial production of ammonia. It is possible that these parameters can be tuned to yield an overall higher efficiency for production of ammonia for support of a bioreactor than those which are used for industrial ammonia production. The reactor may comprise any catalyst as described above with respect to the catalyst for the Haber reactor 250.

One modification to the normal operation of the Haber reactor 250 is to change the ratio of nitrogen to hydrogen provided into the Haber reactor 250. Normally in the Haber process the molar ratio of $N_2$ to $H_2$ is 1 to 3, in line with the stoichiometry of the reaction. In some embodiments of the present invention, the ratio of $N_2$ to $H_2$ may be between 1:3.1 and 1:10, or between 1:10 and 1:100, or between 1:100 and 1:1000, or between 1:1000 and 1:10000, or between 1:10,000 and 1:1,000,000.

Figure 3:
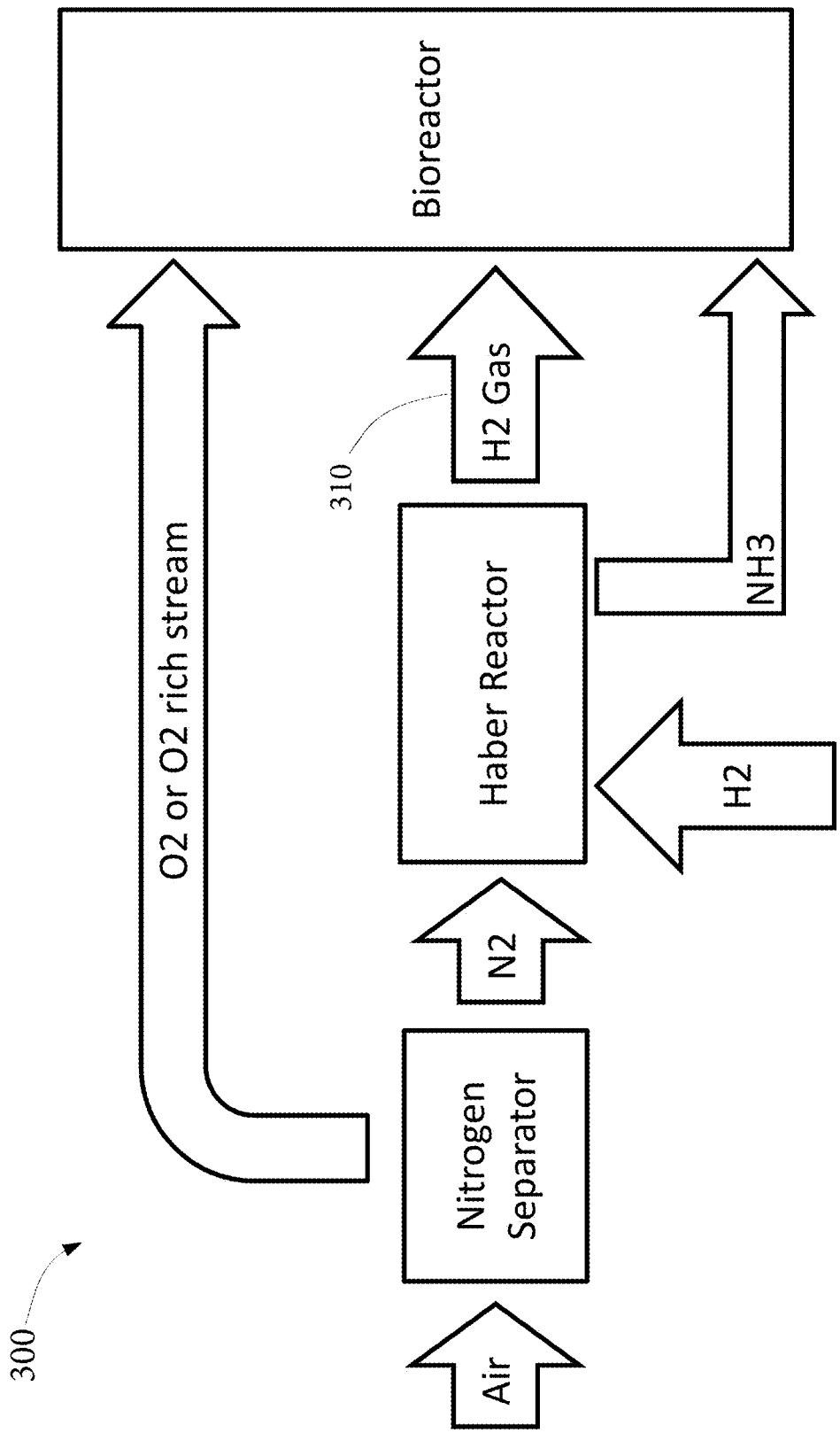
FIG. 3 is a schematic representation of another exemplary system according to various embodiments of the present invention.

Decreasing the amount of nitrogen relative to the amount of hydrogen entering the reactor 250 favors a more complete reaction of the nitrogen fraction into ammonia and thus reduces the amount of unreacted nitrogen in the unreacted stream while it increases the amount of unreacted hydrogen therein, making the unreacted stream more suitable for introduction into the bioreactor 270 as a source of hydrogen (see FIG. 3). Though the presence of nitrogen gas is not normally deleterious to the bioreactor 270, and in certain cases may provide a benefit, the nitrogen gas in some cases will pass through the bioreactor 270 and can also accumulate in the headspace of the bioreactor 270. The presence of unreacted nitrogen in the headspace of the bioreactor 270, or in pass through gas, will increase as headspace gases are recycled and this effect may necessitate occasionally purging the nitrogen gas from the headspace.

Controlling the ratio of nitrogen to hydrogen supplied to the Haber reactor 250 can be an element of the control system described herein, and this ratio may be changed depending on the degree of present or projected need for a nitrogen compound, such as $NH_3$, or hydrogen in the bioreactor 270. Normally, the ratio of hydrogen to nitrogen supplied to a Haber reactor is 3:1 on a volume to volume basis, and this results in an output from the Haber reactor 250 of an unreacted gas stream comprising both unreacted hydrogen and unreacted nitrogen. By increasing the ratio of hydrogen to nitrogen to above 3 to 1, the amount of unreacted nitrogen leaving the Haber reactor 250 in the unreacted stream will decrease. In normal operation of a Haber reactor 250, about 15% of the hydrogen and nitrogen react in each pass through, so even in the case of a system operated under conditions different than those used to manufacture ammonia commercially, it may be desirable to recirculate the gases multiple times. However, by having an excess of hydrogen above the normal 3 to 1 ratio of hydrogen to nitrogen it can be guaranteed that the final pass through gas will be very rich in hydrogen and have very little nitrogen. In various embodiments the ratio of nitrogen ($N_2$) to hydrogen ($H_2$) is maintained for at least part of the time at a ratio between 1:4 and 1:10, or between 1:10 and 1:100, or between 1:100 and 1:1000, or between 1:1000 and 1:10000, or between 1:10,000 and 1:1,000,000.

In some embodiments of the invention the pressure in the Haber reactor 250 will be above ambient pressure. Increasing pressure is a well-known and commonly practiced method of favoring the rate of nitrogen fixation in a Haber reactor. In general, commercial Haber reactors are large in size because they are used as a method for producing large amounts of $NH_3$ and other fixed nitrogen products. These systems are often operated at 15 MPa, (2200 psi). In some instances the reaction conditions are much higher, 25 MPA (about 3700 psi), or more, however, constructing large systems with such high pressure capabilities is very expensive. In some embodiments of this invention the smaller size of this Haber reactor 250 will allow operation at higher pressure while maintaining good economics. In some embodiments, the Haber reactor 250 is maintained at a pressure between 75 TO 65 MPA, (11,000 to 9500 PSI), 65 to 55 MPA, (9500 to 8000 psi), 55 to 45 MPA (8000 to 6500 psi), 45 to 35 MPA (6500 to 5000 psi), 35 to 25 MPA (5000 to 3600 psi), 25 to 15 MPA, (3600 to 2000 psi), 15 to 5 MPA, (2000-800 psi), or 5 to 0.2 MPA (800-30 psi). In some embodiments pressure increases or decreases are used to increase or decrease the rate of reaction. These increases or decreases can be facilitated by high pressure introduction of gases, compression of gases in the reactor, or other means. The reaction of the formation of $NH_3$ from hydrogen and nitrogen is exothermic, and this release of energy may be used to increase the pressure of the reaction gas mixture via increased heat or other means.

Normally the Haber reactor 250, will be operated to react most of the nitrogen, often over 98% of the nitrogen. In this system there will be an excess of hydrogen and thus the nitrogen will react almost completely and the final pass though gas from the Haber reactor 250 will have less than 5% residual nitrogen but still contain additional hydrogen. The increased hydrogen in the mix will shift the reaction equilibrium towards ammonia formation and this can allow the Haber reactor 250 to be operated at lower temperature or pressure. Lower temperature or pressure will greatly slow the Haber reaction to form $NH_3$ but will also allow for increased efficiency. In some embodiments the temperature of the reaction will be maintained between 500° C. and 400° C., 400° C. and 300° C., 300° C. and 200° C., 200° C. and 100° C., 100° C. and 30° C., 30° C. and 25° C., or 25° C. and 0° C. In some embodiments the residency time in the Haber reactor 250 will be increased relative to the residency time in a commercial system. It should also be noted that residual nitrogen in the gas exiting the Haber reactor 250 which is later introduced into the bioreactor 270 will not have a deleterious effect on the bioreactor process as the microbes are tolerant of nitrogen and in some cases capable of biological nitrogen fixation.

Because the reaction of $H_2$ and $N_2$ to produce ammonia is exothermic, the temperature in the Haber reactor 250 can be increased by retaining the heat produced by the reaction in the reactor 250. By operating the reactor 250 in a cyclical manner where the $H_2$ and $N_2$ are introduced and then allowed to react exothermically to produce heat in the reactor 250, it is possible to modulate the fraction of the gases which react. By operating the reactor 250 in a cycle where $H_2$ and $N_2$ are first introduced into the reactor 250 and the ports of the reactor 250 are at least partially closed, then the gases are allowed to react exothermically to produce heat in the reactor 250 whereupon a desired fraction of the gases react, then the output port of the reactor 250 is at least partially opened. The remaining unreacted gases are either conveyed to the bioreactor 270, recycled or vented, and the $NH_3$ formed is removed from the reactor 250 and utilized as described above. Likewise, the above cyclical operation can be configured to allow an increase in pressure which is at least in part due to the increase in heat of the system and its effect on the gases, including the input gases and the ammonia which is formed. The pressure formed in the reactor 250 can be used in the cycle to vent the gases from the reactor 250 and to expel the ammonia.

Figure 11:
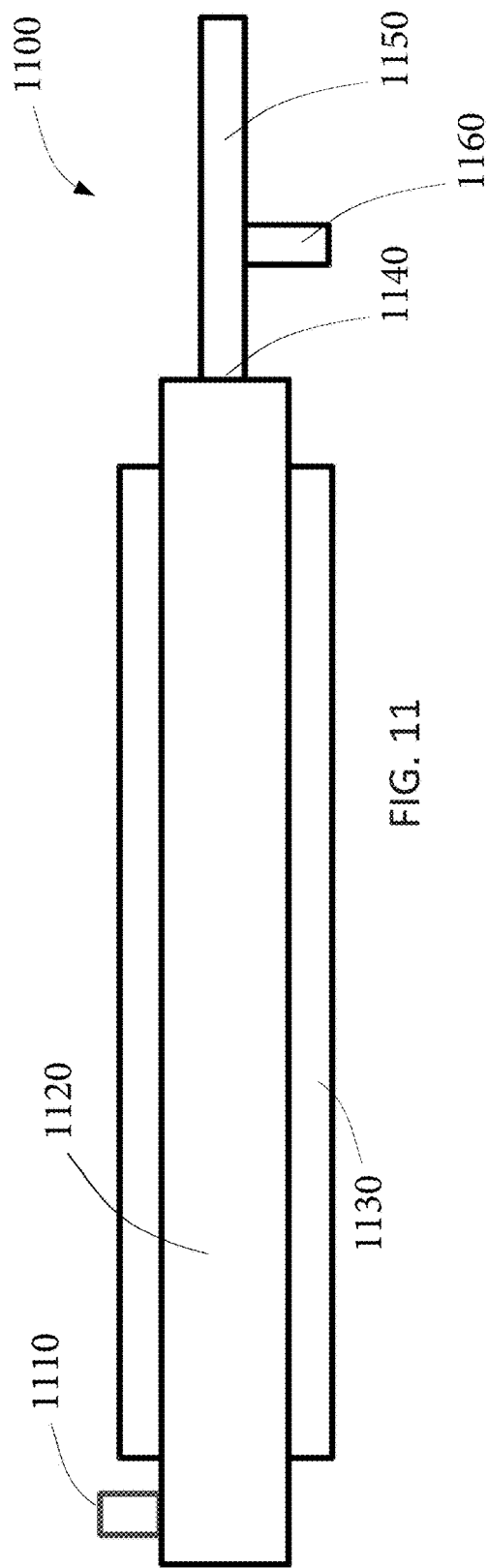
FIG. 11 is a schematic representation of an exemplary tubular reactor according to various embodiments of the present invention.

In some embodiments a tube furnace type arrangement can be employed where a tubular reactor shaped like a pipe is configured to receive a stream comprising nitrogen gas, and where the tubular reactor is configured to receive a stream comprising hydrogen gas, and where the tubular reactor is thermally insulated (see FIG. 11). At least some of the $H_2$ and $N_2$ are reacted within the tubular reactor to product $NH_3$. In some embodiments the tubular reactor may comprise a catalyst. In some embodiments the tubular reactor may be followed by a cooling chamber, which may be a section of pipe, or a vessel, where the temperature of the products is allowed to decrease, or where the temperature is reduced via removal of heat via chilling or other heat reduction, and where the heat may be reduced via reduction of pressure of the gases. Liquid ammonia condenses in the cooling chamber and may be then released, in some embodiments, via the opening of a valve, and may then be collected and used, such as by introduction into the bioreactor, stored for later use in the bioreactor, or diverted for other uses. The pass-through gases may be vented, recycled back into the tubular reactor or introduced into the bioreactor.

In some embodiments a steam methane reformer (SMR) may be used to produce the hydrogen 260 for the process. SMR is a well understood and widely practiced technique and a dominant technology for industrial hydrogen production. In SMR, methane reacts with steam under 3-25 bar pressure (1 bar=14.5 psi) in the presence of a catalyst to produce hydrogen, carbon monoxide, and a relatively small amount of carbon dioxide. The steam reforming reaction is endothermic, i.e. heat must be supplied to the process for the reaction to proceed.

In a "water-gas shift reaction" carbon monoxide and steam are reacted using a catalyst to produce carbon dioxide and hydrogen. The water-gas shift reaction can be applied to the products of the steam methane reformation reaction to yield still more hydrogen and to convert the carbon monoxide to carbon dioxide. In a final process step the products of the water-gas shift reaction are provided to a separator (analogous to the nitrogen separator 220) to remove the carbon dioxide, and any other impurities, from the gas stream, leaving essentially pure hydrogen. The chemical reactions for steam methane reformation and the water-gas shift reaction are shown below:

Steam Methane Reforming Reaction $CH_4+H_2O(+\text{heat})\rightarrow CO+3H_2$

Water-Gas Shift Reaction $CO+H_2O\rightarrow CO_2+H_2(+\text{small amount of heat})$ The $CO_2$ removed from the hydrogen stream in the water-gas shift reaction can at least partially be used as a source of $CO_2$ for carbon fixing microbes in the bioreactor 270 by being conveyed into the bioreactor 270. Because the final separation of $CO_2$ from the hydrogen stream has a cost associated with it, in cases where the microbes in the bioreactor 270 require both hydrogen and $CO_2$, it is possible to divert a stream of mixed hydrogen and $CO_2$ to the bioreactor 270 to supply both $CO_2$ and hydrogen before the $CO_2$ removal step has been completed. Pressure swing adsorption (PSA) is commonly used to remove $CO_2$ or other non-hydrogen gases from syngas mixtures. The method works by introducing, for instance, a mixture of $H_2$ and $CO_2$ into an adsorption system that preferentially traps the $CO_2$ in a porous material such as a zeolite, which may have a metal organic framework element, or by another means, thus allowing a hydrogen enriched stream to pass through. The adsorbed $CO_2$ is then released to produce a second stream predominantly of $CO_2$, however, this second gas stream still may retain some hydrogen and can thus be used similarly to the gas streams mentioned above.

The system 300 of FIG. 3 is similar to that described in FIG. 2 but also provides hydrogen to the bioreactor 270 for the cultivation of hydrogen-oxidizing microbes. In methods of the invention in which hydrogen-oxidizing microbes are cultivated, the microbes consume hydrogen for at least some of their sustenance. In some embodiments, that hydrogen comes from the unreacted stream 310.

In further embodiments, hydrogen introduced into the bioreactor 270 can also comprise hydrogen which did not pass through the Haber reactor 250. Such hydrogen can come from a common source that also feeds the Haber reactor 250, but provides a stream of hydrogen to the bioreactor 270 that bypasses the Haber reactor 250, or the hydrogen can come from an independent second source. In practice, when growing hydrogen-oxidizing microbes, the hydrogen input to the bioreactor 270 is sometimes mixed with carbon dioxide and oxygen, however for the sake of clarity this description omits steps of mixing or introducing other gases, and the analogous structures that facilitate the monitoring and control of the mixing and use. Systems where these further gases are mixed are intended to be included in this invention. Likewise this invention also includes systems where hydrogen is added as an aid to the fermentation of heterotrophic substrates, or, where hydrogen is first reacted, often with $CO_2$, to produce formate, acetate, methanol or another energy rich molecule which are then fermented in a system which also requires a source of fixed nitrogen.

It should also be noted that hydrogen is sometimes added to reaction mixtures used for other types of gas fermentation such as carbon monoxide oxidizing bacteria and methane oxidizing bacteria. Since all of these chemoautotrophic fermentation methods require nitrogen which can be added in the form of ammonia, the integration of a Haber reactor 250 with any of these chemoautotrophic fermentation systems to supply necessary nitrogen is also within the scope of this invention.

Figure 4:
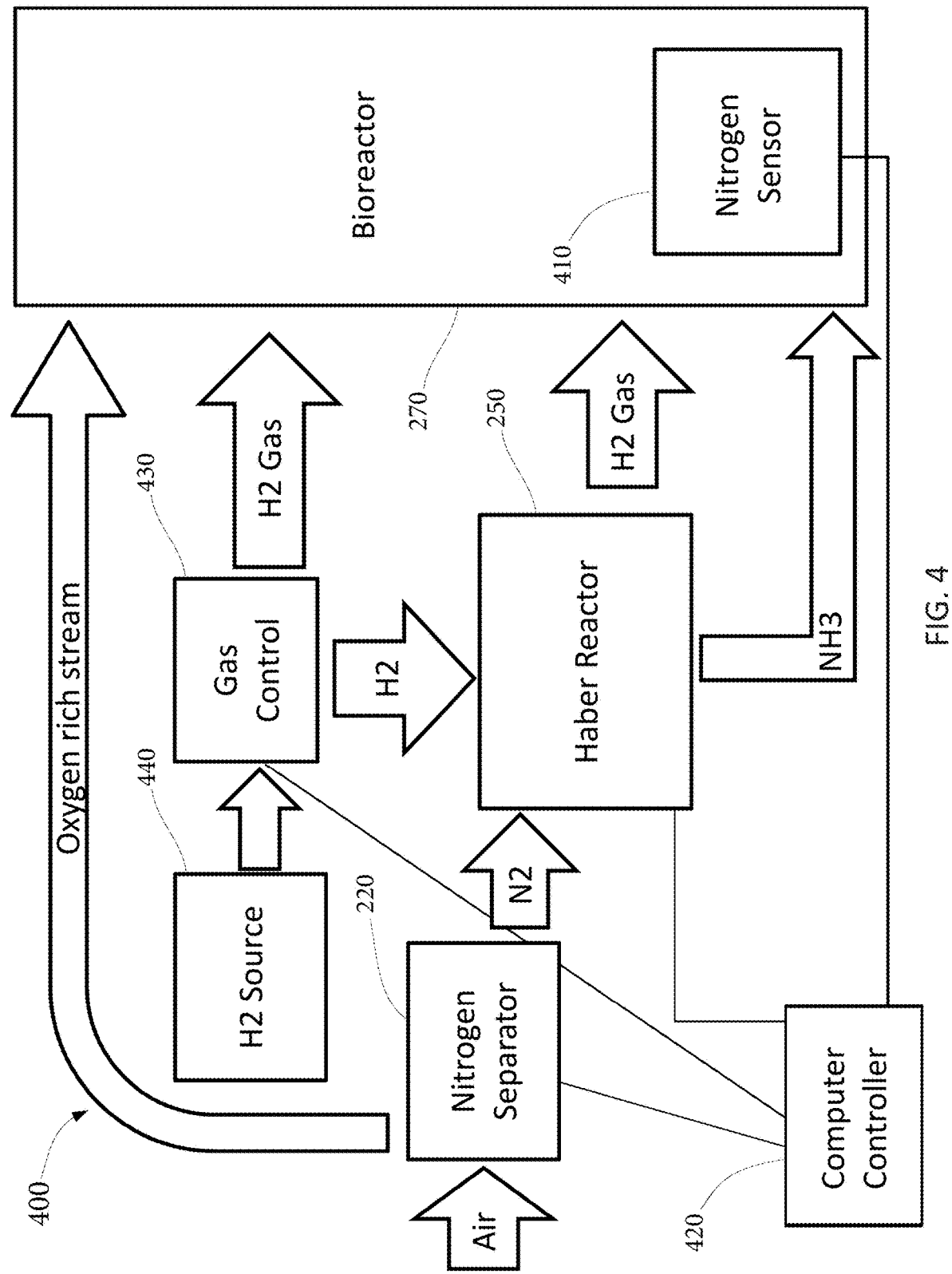
FIG. 4 is a schematic representation of another exemplary system according to various embodiments of the present invention.

System 400 of FIG. 4 is similar to that described with reference to FIG. 3. System 400 further includes at least one nitrogen sensor 410 disposed within the bioreactor 270, or exterior to the bioreactor 270 and in fluid communication with the interior of the bioreactor 270, and a computer-based control system 420 configured to take sensor readings from the nitrogen sensor 410 and use this data to control the operation of the various system elements. The nitrogen sensor 410, in various embodiments, can be any sensor or sensor system which can detect nitrogen or nitrogen containing compounds including chemical reaction based sensor systems, Raman spectrometers, gas chromatographs, electrochemical probes or any other method or system for measuring nitrogen or its various species including $NH_3$, urea, $NO_3$, etc. In this illustration the computer-based control system 420 comprises a computing system such as a PC or server, or programmable logic controller, having a processor and running an executable program in order to control various elements of the system, including regulating the flow of hydrogen 260 to the Haber reactor 250 and to the bioreactor 270, in order to achieve a desired condition such as maximum hydrogen utilization efficiency, maximum microbe growth efficiency, minimum environmental impact, or any other metric or set of metrics.

The computer-based control system 420 also comprises memory, such as random access memory (RAM), to store information including the executable program, received data, and a log of commands sent to systems, like the nitrogen separator, and controllers such as gas flow regulators. Some or all of the computer-based control system 420 can be implemented in firmware or hardware. The computer-based control system 420 includes interfaces with which to take in manual instructions, external data, and sensor readings, and to output control signals and to display an operational status to operators. Computer-based control systems 420 of the invention are described in greater detail with respect to FIG. 4.

The system of FIG. 4 further comprises a gas control unit 430, such as a gas manifold, in fluid communication with a hydrogen source 440 and both of the Haber reactor 250 and the bioreactor 270. The gas control unit 440 receives control signals from the computer-based control system 420 to regulate the amount of hydrogen delivered to the bioreactor 270 and to the Haber reactor 250. The computer-based control system 420 can also be in electrical communication with the Haber reactor 250 and the nitrogen separator 220 in order to regulate either or both. For example, a detected drop in the concentration of nitrogen in the bioreactor 270 below a threshold can be corrected by the control system 420 by increasing the supplies of nitrogen and hydrogen into the Haber reactor 250 and/or by changing the operating conditions of the Haber process by varying temperature and/or pressure, gas flow rate, gas composition, actuating of valves which control the entrance or egress of gases or liquids in the reactor, and or residence time.

In some embodiments, the nitrogen sensor 410 measures, either continuously or periodically, the concentration of nitrogen in the bioreactor 270. The nitrogen sensor 410 is configured to sense one or more nitrogen compounds, including ammonia, urea, nitrates or any other form of nitrogen. Nitrogen sensors 410 can be placed within the liquid medium, in the gas headspace above the medium, within input ports and output ports, within liquid and gaseous effluent streams, and so forth.

Figure 5:
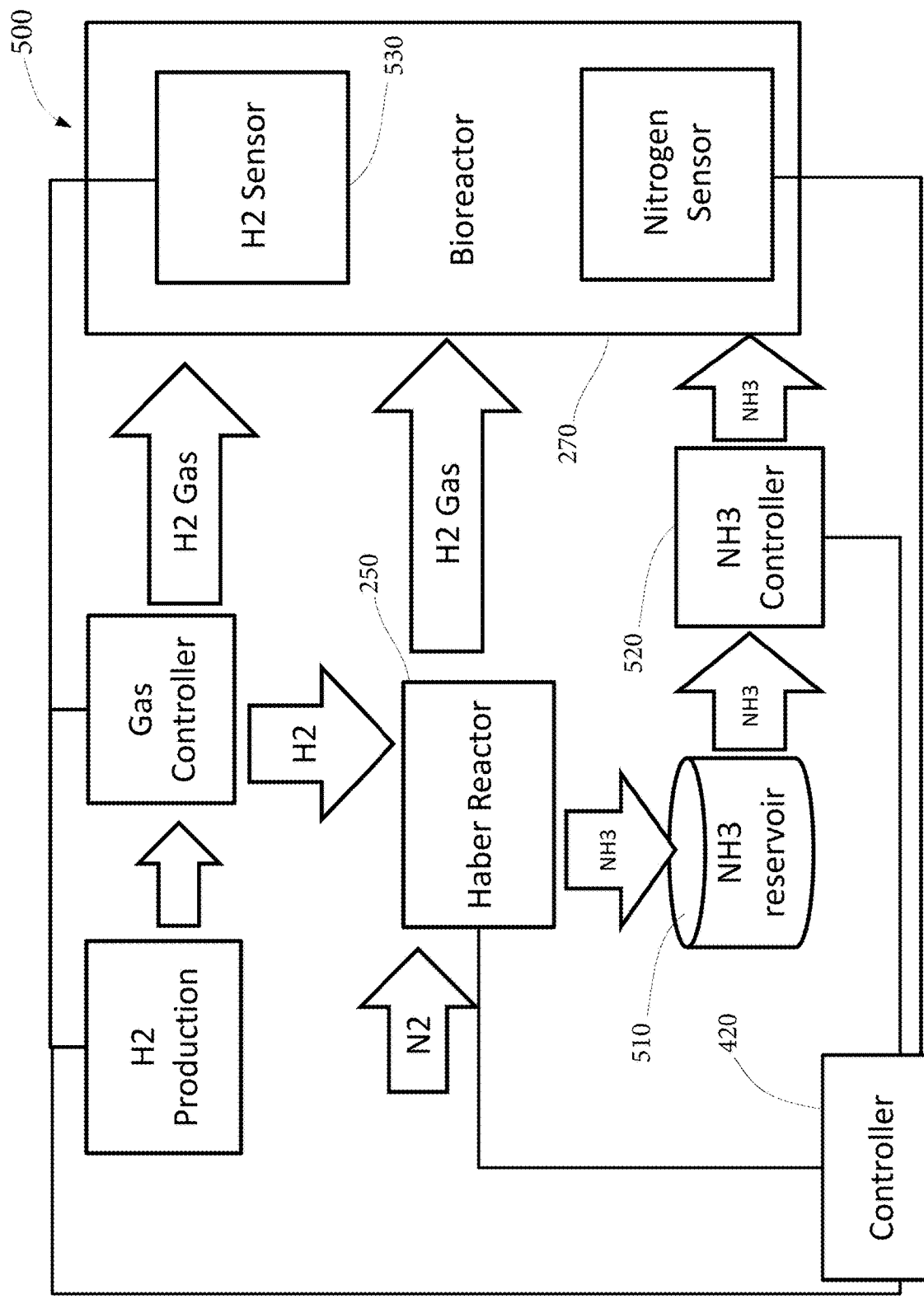
FIG. 5 is a schematic representation of another exemplary system according to various embodiments of the present invention.

System 500 of FIG. 5 is similar to system 400 of FIG. 4. System 500 further includes an ammonia reservoir 510 and an ammonia controller 520 in fluid communication between the Haber reactor 250 and the bioreactor 270. The reservoir 510 receives ammonia from the Haber reactor 250 and the controller 520 regulates the flow of ammonia from the reservoir 510 into the bioreactor 270 under the control of the computer-based control system 420.

The system 500 of FIG. 5 also includes at least one hydrogen sensor 530 disposed within the bioreactor. The computer-based control system 420, in these embodiments, also receives sensor readings from the hydrogen sensor 530 and employs both the hydrogen and nitrogen readings to determine how to regulate hydrogen production, hydrogen flows to the Haber reactor 250 and bioreactor 270, the operating conditions in the Haber process in the Haber reactor 250, and the flow of ammonia into the bioreactor 270 from the reservoir 510.

Because the demand for nitrogen in the bioreactor 270 is related to the population of microbes in the bioreactor 270, their growth rate and other factors, the demand for nitrogen varies over time. Therefore, the amount of nitrogen that will need to be supplied will also vary over time. Because there is a delay in time between when the demand for nitrogen exceeds the available nitrogen in the bioreactor 270 and the ramp-up time of the Haber reactor 250 (i.e., the time to change the conditions in the Haber reactor 250 to those favorable for ammonia production, plus the time to actually produce sufficient ammonia and supply it to the bioreactor 270), it is highly beneficial to the system 500 to have this reservoir 510 of ammonia available for ready delivery, and to recharge the reservoir 510 when most economical to do so.

Figure 6:
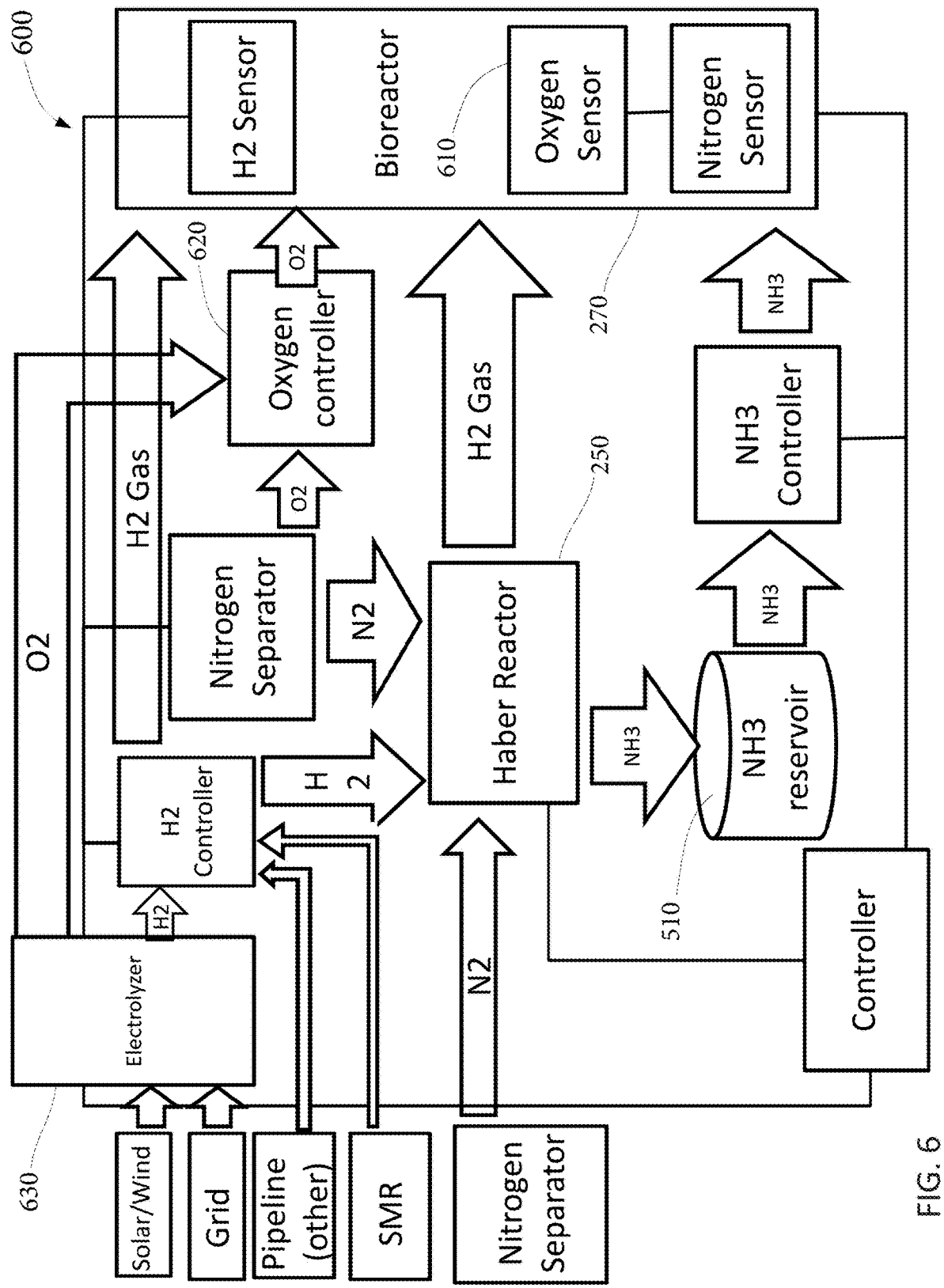
FIG. 6 is a schematic representation of another exemplary system according to various embodiments of the present invention.

The system 600 of FIG. 6 is similar to that described with reference to FIG. 5. System 600 further includes at least one oxygen sensor 610 disposed within the bioreactor 270 and in electrical communication with the computer-based control system 420. The system 600 further still includes an oxygen controller 620 in fluid communication between a source of oxygen, here an electrolyzer 630, and the bioreactor 270 and under the control of the computer-based control system 420 to regulate the flow of oxygen into the bioreactor 270. It will be appreciated that the electrolyzer 630 here serves as an example of a suitable water splitting method to yield oxygen and hydrogen, but other suitable water splitter systems can be used. These include thermally driven systems, plasma systems, nuclear, chemical or catalytic systems, including those employing biological or enzymatic catalysts, and selectively permeable membranes. Further, another potential oxygen source is the residual gas resulting from separating nitrogen from the air. Oxygen from the electrolyzer 630 and from the nitrogen separation process can optionally be combined in a reservoir before being introduced into the bioreactor 270. The two instances of a nitrogen separator in FIG. 6 is done for clarity, and is not meant to imply that two such separators are required.

System 600 also comprises an exemplary source of hydrogen, here again, the electrolyzer 630. The electrolyzer 630 optionally receives electricity from one or more sources. In various embodiments an electricity source can be part of the system 600, such as when solar electricity generation is employed. The solar generation can be thermal or photovoltaic, for example. Similarly, other renewable sources such as wind turbines can be part of the system to provide electricity to the electrolyzer 630, as well as to other electricity consuming processes within the system 600. On-site generation can also come from non-renewable sources in addition to, or in the alternative, such as from diesel generators.

In some embodiments, the electricity for the electrolyzer 630 is instead purchased from an electricity provider such as the public utility grid. In further embodiments, electricity purchased from an electricity provider supplements electricity generated by the system 600 when either the system 600 cannot produce enough electricity to meet its own needs or the cost of electricity is priced below the cost to produce electricity on site.

In some embodiments the $NH_3$ may be stored in a reservoir and if a condition arises where hydrogen is in limited supply, or, the cost of producing hydrogen is high, the $NH_3$ may be reacted to produce $N_2$ and $H_2$, where the $H_2$ can then be fed into the bioreactor 270 and the $N_2$ released, or the mixed $H_2$ and $N_2$ supplied to the bioreactor as a mixed gas, as discussed above. This reaction is endothermic so it can be used to provide cooling functions, such as to cool the bioreactor 270.

In other embodiments, in place of electrolyzer 630, concentrated solar may be used to drive a thermally driven splitting of water, which may also employ a catalyst. In this case the system 600 may take in or be supplied external data such as weather forecasts, season of year or other information to determine the availability of sufficient solar energy and this information, as well as information about competing demands, to determine how much hydrogen and ammonia to produce and store to satisfy current and forecasted needs as well as needs for other processes.

FIG. 6 also illustrates that in some embodiments hydrogen can be supplied by a pipeline from a hydrogen producer, and/or the system 600 can comprise a steam methane reformer (SMR) to supply hydrogen from a natural gas feedstock. In these embodiments, the computer-based control system 420 also receives sensor readings from the oxygen sensor 610 and employs all of the oxygen, hydrogen, and nitrogen readings to determine how to regulate hydrogen production, hydrogen flows to the Haber reactor 250 and bioreactor 270, the Haber process in the Haber reactor 250, and the flow of ammonia into the bioreactor from the reservoir 510. It is noted that systems of the present invention can include more than one source of hydrogen, and can optionally switch between them according to favorable economics.

It will be appreciated that "SMR" in the drawing of FIG. 6 serves to represent a chemical processing system having the ability to perform a steam methane reformation reaction, the ability to perform a water-gas shift reaction on the products of the steam methane reformation reaction, and the ability to separate the products of the water-gas shift reaction into a hydrogen stream and a $CO_2$ stream. Only the hydrogen stream is represented in FIG. 6 flowing to the hydrogen controller, the $CO_2$ stream has been omitted for clarity. Although not shown in FIG. 6, additional carbon monoxide can be produced by a gasifier capable of receiving a carbon-containing substrate such as municipal solid waste, plastic waste, coal, petroleum, natural gas, hydrocarbons, biomass, textile waste, food waste, sewage, medical waste, chemical waste, byproducts, or any other carbon rich feedstock suitable as a gasification substrate to produce a gas stream including carbon monoxide. The CO gas stream can be reacted with water by the water-gas shift reaction to also produce a stream of hydrogen and $CO_2$. Alternately, the CO gas stream from the gasifier can be added to the output of the steam methane reformation reaction and the combined streams then subjected to the water-gas shift reaction.

Figure 7:
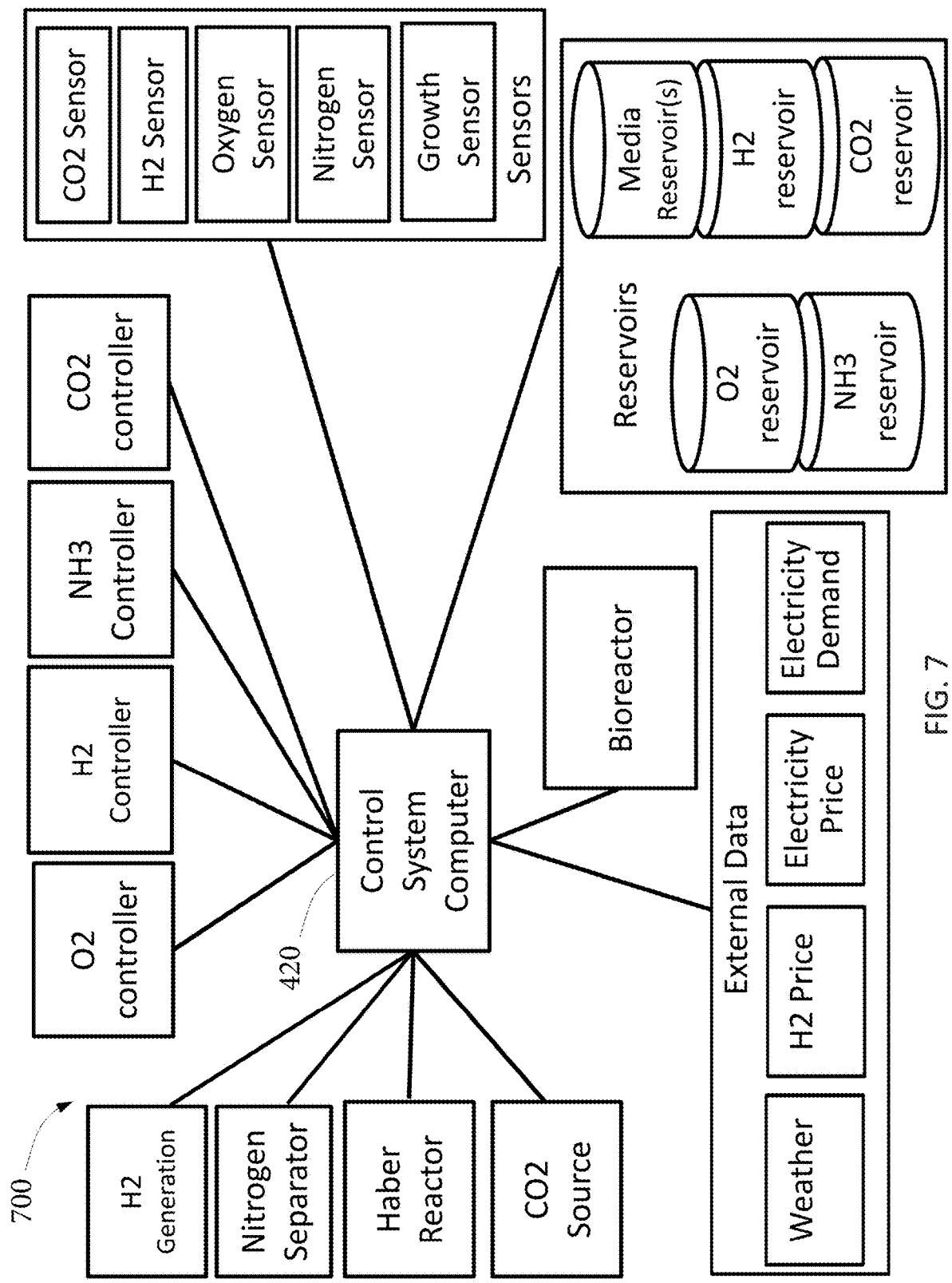
FIG. 7 is a schematic representation of another exemplary system according to various embodiments of the present invention.

FIG. 7 illustrates an exemplary control system 700 of the present invention that extends the embodiment of FIG. 6 to include a source of $CO_2$, a $CO_2$ controller in fluid communication between the source and the bioreactor, and at least one $CO_2$ sensor disposed within the bioreactor and in electrical communication with the computer-based control system 420, where the computer-based control system 420 includes instructions that can be executed by the processor to regulate a flow of $CO_2$ into the bioreactor based on readings from the $CO_2$ sensor, alone or in combination with readings from other sensors in the bioreactor. In various embodiments the source of $CO_2$ can be a $CO_2$ stream from an SMR as described with respect to FIG. 6, or can be from another source, like a commercially delivered $CO_2$ tank.

The system 700 of FIG. 7 extends that of FIG. 6 to also include one or more growth sensors disposed within the bioreactor and configured to monitor the rate of growth and/or the concentration of microbes in the medium, for instance an optical density sensor which measures cell density in the medium. The system 700 of FIG. 7 further extends that of FIG. 6 to include reservoirs for any or all of ammonia, oxygen, hydrogen, $CO_2$, and additional liquid medium.

As shown in FIG. 7, the computer-based control system 420 can be configured to control any or all of a hydrogen generation system, an air separation system for supplying nitrogen, a Haber reactor, a $CO_2$ source, and a bioreactor. The computer-based control system 420 can be further configured to control any or all of an oxygen controller, a hydrogen controller, an ammonia controller, and a $CO_2$ controller to regulate flows of these into the bioreactor. The various controls can be based on information received by the computer-based control system 420 from any or all of the sensors disposed in the bioreactor, sensors that measure the amount stored in any of the reservoirs (such as float sensors for stored liquids and pressure sensors for stored gases), and external data. External data can comprise any or all of weather forecast data, electricity demand projections, and current and projected prices for commodity consumables such as electricity and hydrogen.

Figure 8:
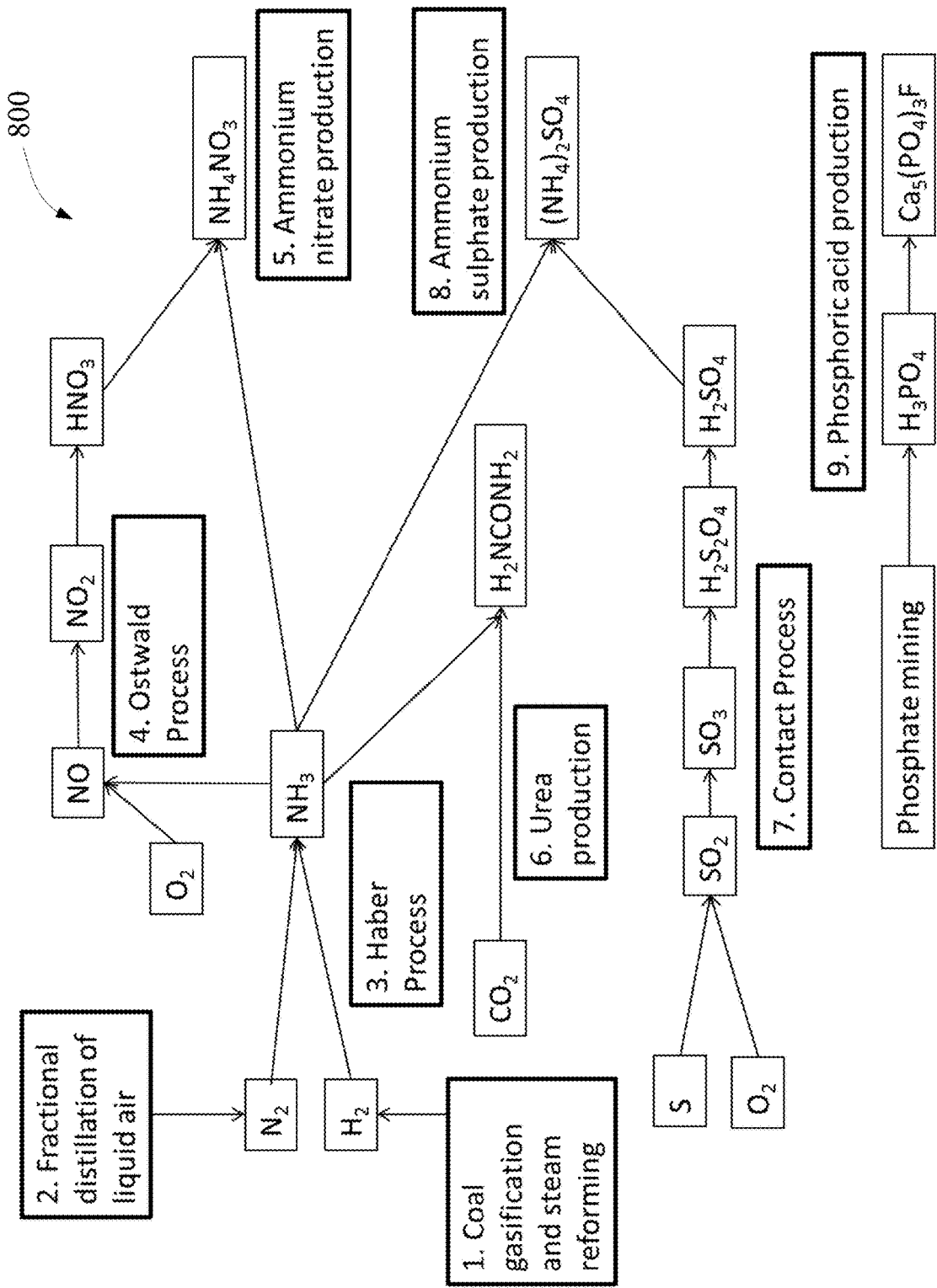
FIG. 8 is a schematic representation of another exemplary system according to various embodiments of the present invention.

FIG. 8 is a schematic representation of an exemplary system 800 of the present invention, the bioreactor omitted for clarity, including a number of processes that can further employ ammonia produced by the nitrogen fixation method. FIG. 8 shows the production of urea from ammonia and $CO_2$. FIG. 8 also shows the production of nitric acid by the Ostwald process, using ammonia and oxygen, such as from electrolysis. FIG. 8 further shows the further production of ammonium nitrate from the nitric acid and further ammonia. FIG. 8 shows further still the production of sulfuric acid from a source of sulfur and oxygen, such as from electrolysis, according to the Contact process and the further manufacture of ammonium sulphate from the further reaction of sulfuric acid with ammonia. Lastly, FIG. 8 illustrates the production of phosphoric acid from mined phosphorous deposits, and the further reaction of phosphoric acid with calcium and fluorine to create fluorapatite.

Figure 9:
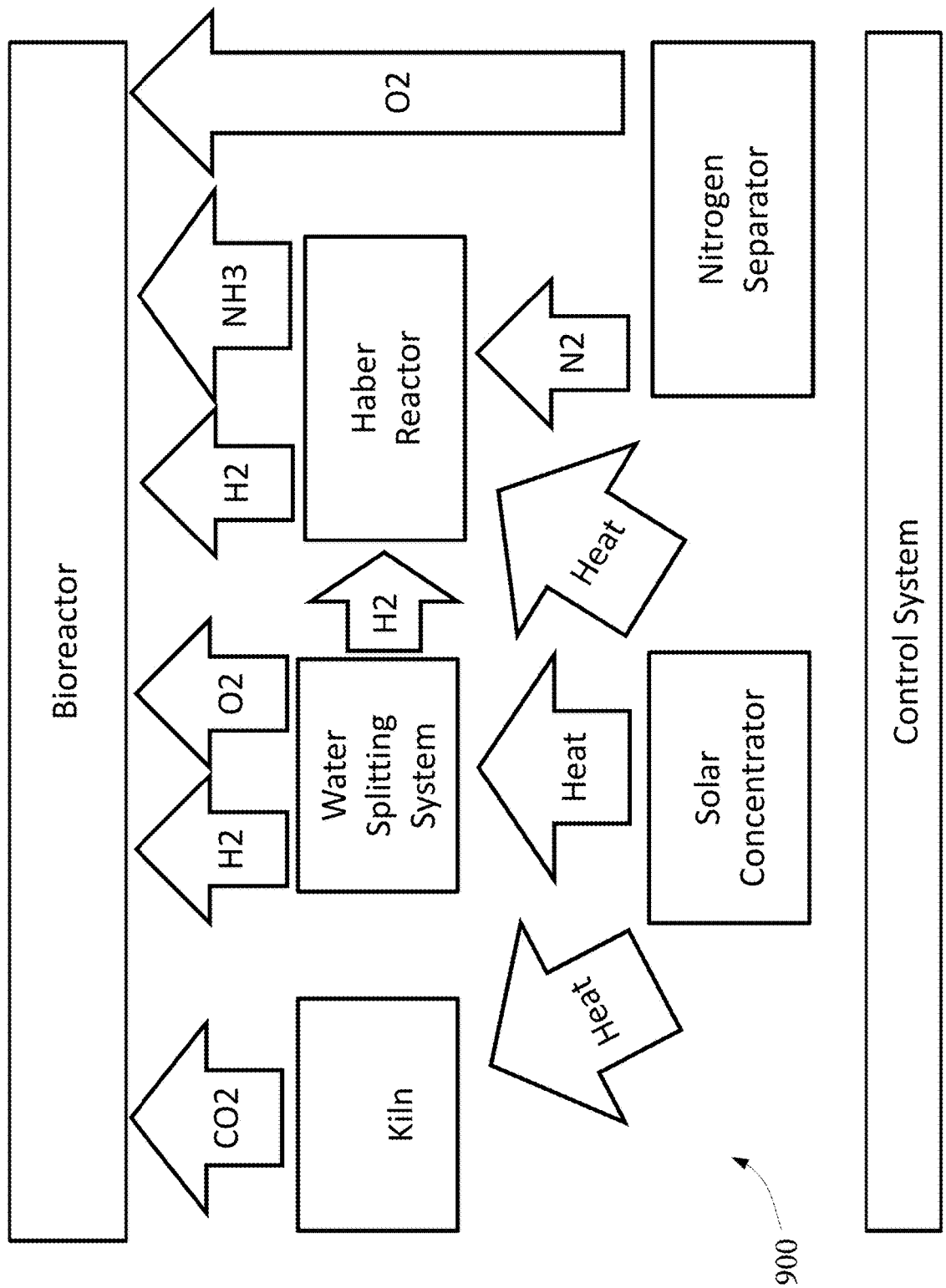
FIG. 9 is a schematic representation of another exemplary system according to various embodiments of the present invention.

The process of making cement and quicklime, as well other mineral processing activities produces a great deal of $CO_2$ and requires a great deal of energy. These processes produce $CO_2$ from both the combustion of fuels to provide needed heat and as a part of the chemical process of product creation. FIG. 9 shows an exemplary system 900 applied to the production of cement, quicklime or other process wherein a mineral substrate, such as calcium carbonate, or limestone containing $CaCO_3$ is heated in a kiln process to produce CaO mineral product and $CO_2$ gas. In this example concentrated solar is used to produce the heat in the kiln. The concentrated solar heat may also be used to supply heat to a thermal catalytic reactor capable of splitting of water into oxygen and hydrogen streams, and may also be used to provide heat to the Haber reactor. At least some of the hydrogen from the water splitting system is directed into the bioreactor, and at least some of the hydrogen is for some period of time directed into the Haber reactor. At least some of the $CO_2$ produced by the reaction of $CaCO_3$ to form cement CaO, is directed into the bioreactor. At least some of the $NH_3$ produced by the Haber reactor is directed into the bioreactor. Oxygen from the oxygen rich stream byproduct of the nitrogen separator upstream of the Haber reactor, and oxygen produced by the water splitting system, may each be to some extent directed into the bioreactor. Excess oxygen may be stored as compressed gas or liquid and if in excess may constitute an additional product. The control system can be configured to manage in real time and/or based on predictions using sensors, historical and outside data, the various flows and functions, storage, sources etc., of the end to end system 900 to optimize cost, carbon footprint, product formation or other desired metrics or outcomes. In FIG. 9, for simplicity the sensors, controllers, and reservoirs are omitted, but as shown above every gas, liquid or material in the system 900 can have one, two or all three of a sensor, a controller, and a reservoir.

Figure 10:
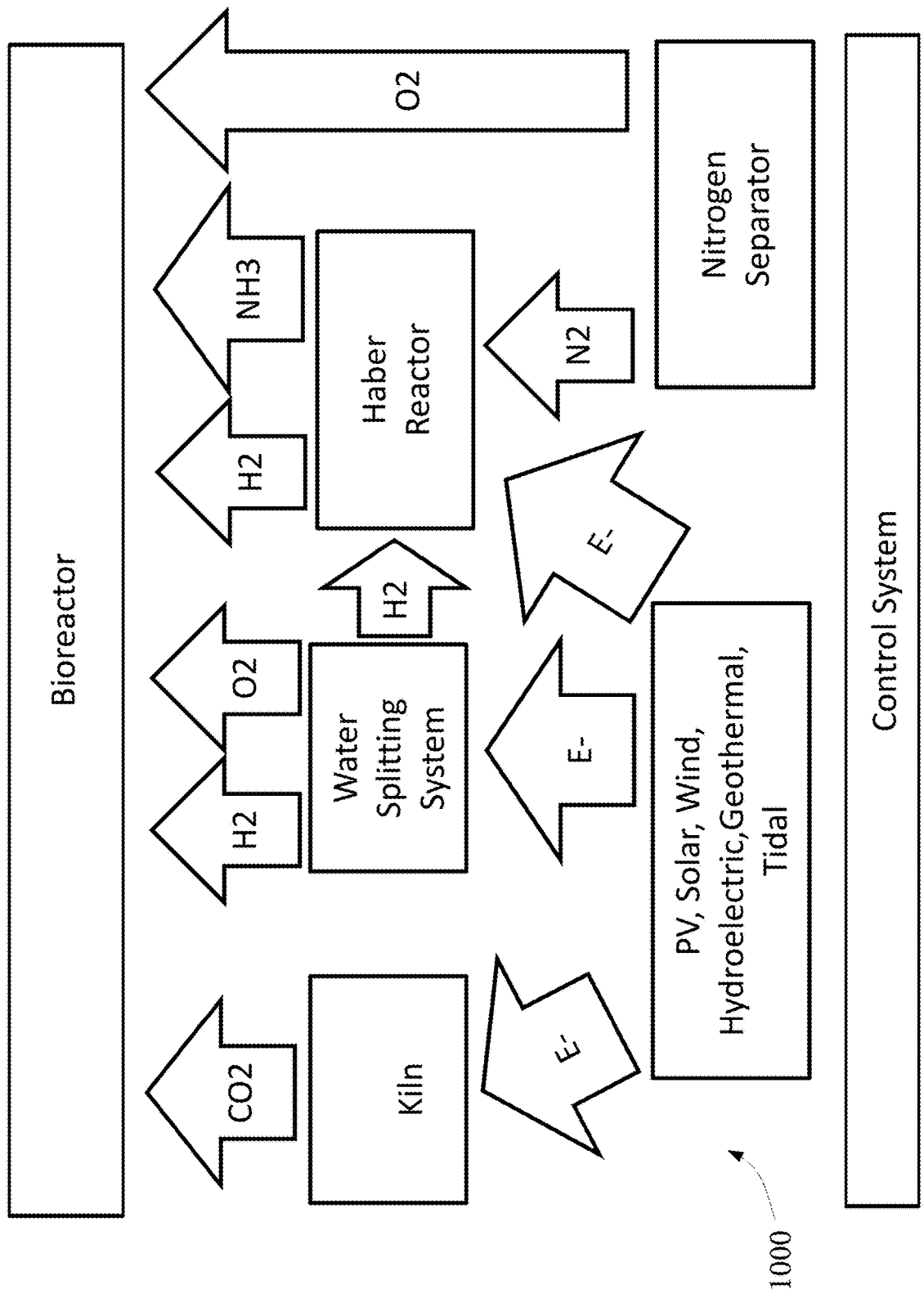
FIG. 10 is a schematic representation of another exemplary system according to various embodiments of the present invention.

FIG. 10 shows a similar system to FIG. 9 however system 1000 employs a renewable energy source to produce electricity. The produced electricity is used to power a water splitting system, in this example an electrolyzer. Electricity produced by system 1000 may also be used to at least partially power the kiln or other processes of the mineral production, and also may at least partially power the Haber reactor or nitrogen separator. In other respects the system 1000 is similar to the system 900 of FIG. 9 in terms of sensing, control and reservoirs.

FIG. 11 provides a cross-sectional view of an exemplary tubular furnace reactor 1100. The reactor 1100 comprises at least one input port 1110 for $H_2$ and $N_2$ gas, a tubular section 1120 wrapped with insulation 1130 to retain at least part of the heat generated by the exothermic formation of $NH_3$ from $N_2$ and $H_2$. The reactor 1100 further comprises an exit port 1140 from which gases are released from the tubular reactor 1100, and a condensation chamber 1150 that condenses the $NH_3$ fraction as a liquid which is removed through port 1160. In some embodiments the condensation chamber 1150 may be a tube. In some embodiments, in place of the condensation chamber 1150, the reactor 1100 can include a separator which separates the $H_2$ and $N_2$ gas streams from the $NH_3$ via a membrane, fractional distillation, adsorption, or another method.

Figure 12:
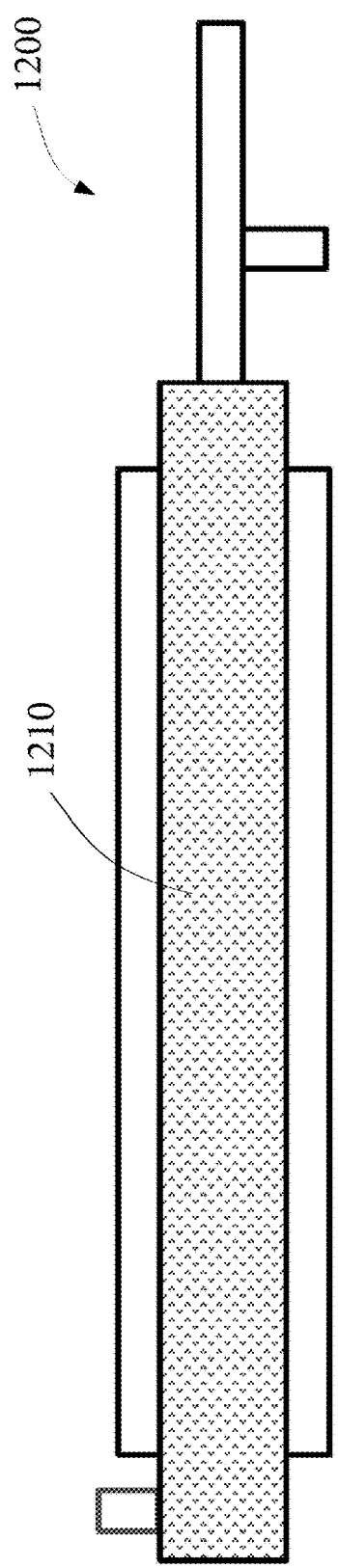
FIG. 12 is a schematic representation of another exemplary tubular reactor according to various embodiments of the present invention.

FIG. 12 shows a reactor 1200 that adds a catalyst 1210 to reactor 1100. The catalyst 1210 is represented in FIG. 12 generically, but in various embodiments the catalyst 1210 may comprise any catalyst as described above with respect to the catalyst for the Haber reactor 250.

Figure 13:
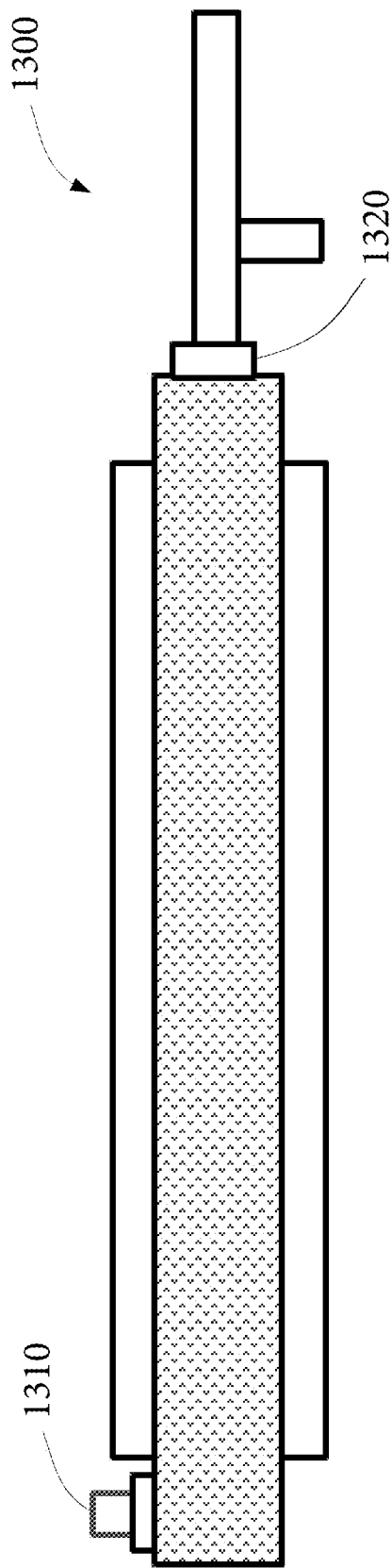
FIG. 13 is a schematic representation of another exemplary tubular reactor according to various embodiments of the present invention.

FIG. 13 shows a reactor 1300 that adds controllable valves 1310, 1320 to the reactor 1200 at the entrance and exit to the tubular section 1120. It will be appreciated that other embodiments do not include the catalyst 1210 while retaining the valves 1310, 1320. In various embodiments the valves 1310, 1320 are controlled independently, while in other embodiments the valves 1310, 1320 are controlled together.

In some embodiments, the tubular reactor 1300 can be operated in a cyclical manner where mixed $H_2$ and $N_2$ gases are introduced into the reactor 1300 via the inlet port 1110. After a period of time, the exit valve 1140 is at least partially closed, or fully closed, and also the inlet valve 1110 is at least partially closed or fully closed. Heat is produced by the reaction to produce $NH_3$ and that heat is substantially retained within the tubular section 1120 by the insulation 1130. In some embodiments this leads to an increase in the pressure inside the tubular section 1120. In some embodiments this leads to an increase in the temperature and pressure inside the tubular section 1120. The exit valve 1140 is opened after a reaction period to allow the mix of unreacted gases and $NH_3$ flow into the condensation chamber 1150. In some embodiments, cooling the gases in the condensation chamber 1150 allows the $NH_3$ to liquefy while the unreacted gases, predominantly $H_2$, remain gaseous. In some embodiments at least part of this cooling is achieved via the endothermic process of gas expansion by modulating the exit valve 1140 to control the corresponding flow of the gases into the condensation chamber 1150.

Figure 14:
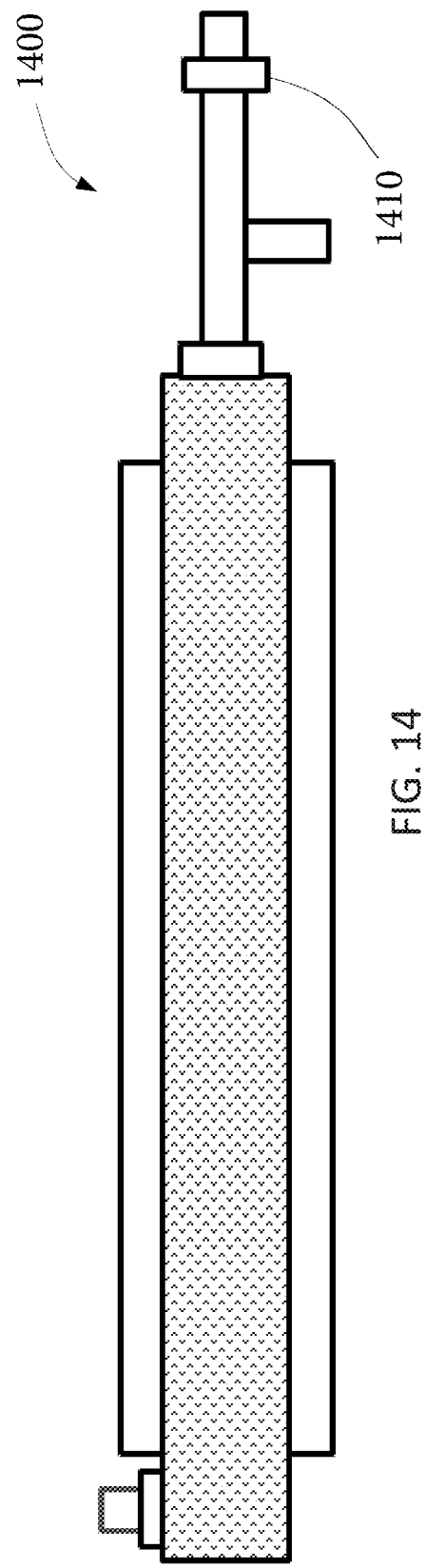
FIG. 14 is a schematic representation of another exemplary tubular reactor according to various embodiments of the present invention.

FIG. 14 shows a reactor 1400 that adds a second exit valve 1410 to the reactor 1300. In reactor 1400 the second exit valve 1410 creates a region between the exit valve 1140 and second exit valve 1410. In some embodiments, gasses are released from the tubular section 1120 through the exit valve 1140 into the condensation chamber 1150 at a pressure and a temperature that are both higher than the ambient. Optionally, the temperature in the condensation chamber 1150 may be higher than ambient, but lower than the temperature within the tubular section 1120. The higher than ambient pressure zone within the condensation chamber 1150 can aid in the condensation of $NH_3$ by increasing the temperature at which ammonia condenses. In some embodiments any gases not condensed in the condensation chamber 1150 are conveyed into the bioreactor 270, or recycled back into the tubular section 1120, vented to atmosphere, combusted, or stored.

Various embodiments of the present invention also comprise a predictive system to allow production to take place when most economical. Thus, a predictive model as part of the computer-based control system can be used herein, for instance, to prepare the air separation system to begin nitrogen production when utility rates are low, or to wait and bypass the cheaper electricity for a day in which sunshine and steady winds are predicted, and to fill the nitrogen and oxygen reservoirs at that time, unless the model predicts that the reservoirs will be drawn down before that predicted day, in which case electricity from the grid could be used sooner. The predictive model can employ machine learning and/or artificial intelligence and be trained over time to better predict bioreactor demands and to match those demands with feedstocks produced most efficiently.

Predicting bioreactor demands can comprise, for example, training the predictive model based on measurements from sensors in the bioreactor that measure the rate of growth and the concentration of microbes in the bioreactor medium over time. A predictive model trained on accumulated microbial population and growth data correlated with nitrogen demand at the bioreactor can allow the overall system to be run with increased efficiency, as well as help ensure that growth rates and concentrations are not impeded by a lack of available nitrogen. Parameters that can be used to train the predictive model include the strain of microbe(s) being cultivated, media composition, temperature, pH, time of day, day of week, price of hydrogen at a given time, price of both grid and renewable electricity, stage of growth of the microbes and a stated or predictive end of the fermentation, external data which can correlate to sensor data such as weather, season, amount of sunlight, cost and availability or competing demands for ammonia, hydrogen, or any other ingredients used by the system.

Accordingly, a predictive model can be used to configure an electrolyzer or other water splitting technology to produce hydrogen at a rate or in an amount needed, or which is predicted to be needed, in order to supply the Haber reactor with adequate hydrogen to support predicted ammonia needs, as well as to supply the bioreactor with adequate hydrogen to support microbial growth. The computer-based control system can be configured to optimize for a number of parameters including the efficiency of resource utilization, maximum product formation, minimum carbon footprint or a balance of these or other target outcomes.

With regard to the source of hydrogen, there are a number of different ways it can be supplied with variable or fixed costs as well as different carbon footprints, and the like. For example, hydrogen can be provided from a source where the price and availability are set by contract. Hydrogen can also be provided via a number of methods including splitting of water via splitting of water in thermally driven, nuclear and electrolytic processes, by steam methane reformers, water shift reactors or other hydrogen production systems where the cost and availability of hydrogen vary. There are many examples of systems such as these, and by using reservoirs for ammonia produced by the Haber reactor, and for other constituents, the net cost of operating the system can be reduced by refilling the reservoirs when the inputs to the system are cheapest.

A further example is when an electrolyzer is used to produce hydrogen. Here, there is a benefit to producing ammonia when the electricity to run the electrolyzer is cheapest. In many locations electricity is less expensive when used in time periods when overall electricity usage is lower. This is referred to as 'off peak' electricity and thus the system can intelligently use off-peak time periods for hydrogen generation to produce ammonia more cheaply and store this in the reservoir for later use. In a similar way, if electrolytic hydrogen is employed where the electrolyzers are at least partially supplied with electricity from solar or wind power, the system can produce ammonia when there are favorable levels of solar or wind available and thus reduce cost by using less purchased electrical power.

Factors of cost are not the only consideration for how the system operates. Reducing $CO_2$ emissions for a reduced carbon footprint are also goals or performance metrics in which improvements may be sought. As a still further example, hydrogen can be supplied via water splitting, or via steam reformation of methane where some of the methane is produced from biological processes (ie: biogas or green methane), and the rest is a petrochemical. The predictive model can be trained to take into account the current and predicted ammonia requirements of the bioreactor, the $CO_2$ emissions and carbon footprint of each hydrogen source, the overall supply of hydrogen possible from each source, the cost of electricity, the cost of the several methane sources, and derive a dynamic control program which produces the optimal amount of ammonia to satisfy overall goals of lower $CO_2$ emissions and lowest cost.

In some embodiments, in which more than one source of hydrogen is available, the computer-based control system can make decisions about how much from each hydrogen source to use at any given time and dynamically regulate them or switch between them. In embodiments in which the electrolyzer can be powered by more than one electricity source, for example, by each of solar power, wind power, and the grid, the computer-based control system can decide which source to employ. Decisions on hydrogen and electricity usage can be based on availability and costs information derived from external sources. In this way reservoirs can be filled, for instance, when conditions are favorable for inexpensive production.

In some embodiments reducing carbon emissions, or atmospheric carbon may be an important goal. In a specific embodiment with this goal, renewable electricity produced by wind, solar or another low carbon method can be used to power an electrolyzer which provides at least part of the hydrogen for the system. In this type of embodiment, the computer control system may also determine the amount of renewable electricity which is supplied to the electrolyzer system to supply the current and anticipated hydrogen needed for the Haber reactor and the bioreactor. This determination can also take into account the amount of electricity demand due to competing uses of electricity and which use of electricity is best. Hydrogen in excess of what is immediately needed may be stored and used in the future or run through a fuel cell to produce electrical power. The decisions about the best uses of hydrogen, electricity, oxygen, water or other resources used or consumed in the process may be determined by using a hierarchy of rules, at least some of which may be derived by the AI system, and others which may be user input to the system as a part of a rule set. The computer-based control system can balance data from many sources, including sensor input, cost of resources, value of resources if sold elsewhere, cost of purchasing resources, projected availability of resources, amount of stored resources, safety, regulatory and other factors in determining the best distribution of resources at any time.

In some embodiments the heat required by the Haber reactor can be produced by solar or geothermal energy. Temperature sensors in the Haber reactor measure the current temperature and the computer-based control system will use this information in concert with information derived from other sensors in the system such as bioreactor nitrogen sensors, hydrogen sensors and others to determine the heat and pressure to operate the Haber reactor in order to produce the amount of ammonia needed to satisfy current or future demand.

In some embodiments where renewable energy, such as solar, wind, tidal or geothermal is used to supply energy for hydrogen production, whether via creation of electricity, or heat for thermally driven processes, the current and anticipated availability of renewable energy may be used to determine how much ammonia and/or hydrogen to produce or store, and/or how much ammonia or hydrogen to obtain from other sources. The anticipated amount of renewable energy available can be determined at least in part by considering meteorological data, geospatial data, tidal, or other data collected outside of the system, as well as sensor data. This is true for any of the inputs which may vary in cost, availability, carbon footprint or other aspect. In some cases, the purchase of ammonia or hydrogen from suppliers will be facilitated or executed by the control system. A machine learning or artificial intelligence system such as mentioned above may be employed to determine optimized outcomes of production levels by the system, cost, carbon or environmental footprint, or a mix of these. This determination can then be used to adjust the conditions of the Haber reactor, hydrogen production rate, ammonia production, and to modify other conditions of the operation of the various parts of the system to achieve the desired outcome.

The system may be controlled or configured to achieve a desired condition such as maximum hydrogen utilization efficiency, maximum microbe growth efficiency, minimum environmental impact, lowest cost of operation, quality or yield of fermentation product or any other metric or set of metrics. The system can be upgraded via hardware changes, software changes or changes to the controllable elements to improve performance. Upgrades or changes to the system can be made based on the performance of other similar systems which are not in active communication with the control system.

In the foregoing specification, the invention is described with reference to specific embodiments thereof, but those skilled in the art will recognize that the invention is not limited thereto. Various features and aspects of the above-described invention may be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

The invention claimed is:

1. A system comprising: a nitrogen separator that separates air into a nitrogen-rich gas stream and an oxygen-rich gas stream;
a nitrogen fixation reactor in fluid communication with the nitrogen separator to receive the nitrogen-rich stream, and further configured to receive hydrogen, and configured to react nitrogen with hydrogen to produce an ammonia stream; and
a bioreactor comprising a liquid medium including a population of microbes, the bioreactor in fluid communication with the nitrogen fixation reactor to receive a stream of a fixed nitrogen compound derived from the ammonia stream to support growth of the population of microbes; and
wherein the nitrogen separator is in fluid communication with the bioreactor to supply at least some of the oxygen-rich stream produced by the nitrogen separator to the bioreactor.

2. The system of claim 1 wherein the nitrogen fixation reactor produces an unreacted gas stream comprising hydrogen, wherein the nitrogen fixation reactor is in a second fluid communication with the bioreactor to provide at least some of the unreacted gas stream to the bioreactor, and wherein at least some of the microbes of the population comprise hydrogenase enzymes capable of deriving energy through hydrogen oxidation.

3. The system of claim 1 further comprising a control system configured to vary the ratio of hydrogen to nitrogen entering the nitrogen fixation reactor.

4. The system of claim 1 further comprising
a steam methane reformer configured to perform both a steam methane reformation reaction and a water-gas shift reaction to produce a stream including both hydrogen and $CO_2$, and
a separator in fluid communication with the steam methane reformer and configured to separate the stream including both hydrogen and $CO_2$ into a hydrogen stream and a $CO_2$ stream,
wherein the separator is in fluid communication with the bioreactor to provide at least some of the $CO_2$ stream to the bioreactor, and wherein the separator is also in fluid communication with the nitrogen fixation reactor to provide at least some of the hydrogen stream to the nitrogen fixation reactor.

5. The system 1 further comprising
a gasifier configured to gasify a carbon-containing substrate to produce a gas stream including carbon monoxide.

6. The system of claim 1 further comprising a water splitter configured to receive a flow of water and to produce from the water both a hydrogen stream and an oxygen stream, and wherein the water splitter is in fluid communication with the nitrogen fixation reactor to provide at least some of the hydrogen stream to the nitrogen fixation reactor.

7. The system of claim 6 wherein the water splitter is in fluid communication with the bioreactor to provide at least some of the oxygen stream produced by the water splitter to the bioreactor.

8. The system of claim 1 further comprising
a nitrogen sensor disposed within the bioreactor; and
a control system configured to regulate the introduction of ammonia into the bioreactor based on a signal from the nitrogen sensor.

9. The system of claim 8 wherein
the nitrogen fixation reactor is further configured to produce an unreacted gas stream and is in further fluid communication with the bioreactor to provide at least some of the unreacted gas stream to the bioreactor, and
the system further comprises a hydrogen sensor dispersed within the bioreactor and connected to the control system, wherein the control system is further configured, responsive to a signal from the hydrogen sensor in addition to that from the nitrogen sensor, to regulate the nitrogen fixation reactor, and to regulate the introduction of the unreacted gas stream and the stream of the fixed nitrogen compound into the bioreactor.

10. The system of claim 1 further comprising an ammonia reservoir disposed between the nitrogen fixation reactor and the bioreactor.

11. The system of claim 1 wherein the nitrogen fixation reactor comprises an insulated tubular reactor, wherein the bioreactor is additionally in fluid communication with the tubular reactor to receive an unreacted hydrogen stream separately from the stream of the fixed nitrogen compound.

12. The system of claim 11 wherein the tubular reactor includes a first exit valve and a second exit valve at opposite ends thereof.

13. A system comprising:
a kiln used in the production of a mineral product;
a nitrogen fixation reactor configured to produce an ammonia stream and an unreacted gas stream;
a nitrogen separator configured to produce a nitrogen-rich stream and an oxygen-rich stream;
a water splitting system configured to produce a hydrogen stream and an oxygen stream;
a bioreactor comprising a liquid medium including a population of microbes, the bioreactor in fluid communication with the nitrogen fixation reactor to receive a stream of a fixed nitrogen compound derived from the ammonia stream to support growth of the population of microbes; and
a solar concentrator system configured to
provide heat to the kiln,
provide heat to the water splitting system, and
provide heat to the nitrogen fixation reactor, wherein
the nitrogen separator is in fluid communication with the bioreactor to provide at least some of the oxygen-rich stream to the bioreactor, or the water splitting water system is in fluid communication with the bioreactor to provide at least some of the oxygen stream to the bioreactor,
the kiln is in fluid communication with the bioreactor to provide at least some of the $CO_2$ produced by the kiln to the bioreactor,
the water splitting water system is in fluid communication with the nitrogen fixation reactor to provide at least some of the hydrogen stream to the nitrogen fixation reactor, and
the nitrogen fixation reactor is in further fluid communication with the bioreactor to provide at least some of the unreacted gas stream to the bioreactor.

14. The system of claim 13 wherein the water splitting system comprises an electrolyzer, the system further comprising
a renewable electricity source configured to at least partially supply electricity to the kiln, and further configured to supply electricity to the electrolyzer.

* * * * *